(12) United States Patent
Cohen et al.

(10) Patent No.: US 12,296,004 B2
(45) Date of Patent: May 13, 2025

(54) RECOMBINANT VIRUS WITH DIMINISHED LATENCY AND METHODS OF USING SAME

(71) Applicant: The U.S.A., as represented by the Secretary, Department of Health and Human Services, Bethesda, MD (US)

(72) Inventors: Jeffrey I. Cohen, Bethesda, MD (US); Lesley Pesnicak, Stafford, VA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 251 days.

(21) Appl. No.: 17/692,540

(22) Filed: Mar. 11, 2022

(65) Prior Publication Data

US 2022/0193227 A1 Jun. 23, 2022

Related U.S. Application Data

(62) Division of application No. 16/195,247, filed on Nov. 19, 2018, now Pat. No. 11,305,009, which is a division of application No. 12/514,011, filed as application No. PCT/US2007/084331 on Nov. 9, 2007, now Pat. No. 10,166,285.

(60) Provisional application No. 60/857,766, filed on Nov. 9, 2006.

(51) Int. Cl.
*A61K 39/25* (2006.01)
*A61K 39/12* (2006.01)
*A61K 39/245* (2006.01)
*C07K 14/005* (2006.01)
*C12N 7/00* (2006.01)
*C12N 15/86* (2006.01)
*A61K 39/00* (2006.01)

(52) U.S. Cl.
CPC .............. *A61K 39/25* (2013.01); *A61K 39/12* (2013.01); *A61K 39/245* (2013.01); *C07K 14/005* (2013.01); *C12N 7/00* (2013.01); *C12N 15/86* (2013.01); *A61K 2039/5254* (2013.01); *C12N 2710/16022* (2013.01); *C12N 2710/16722* (2013.01); *C12N 2710/16734* (2013.01); *C12N 2710/16743* (2013.01); *C12N 2710/16761* (2013.01)

(58) Field of Classification Search
None
See application file for complete search history.

(56) References Cited

U.S. PATENT DOCUMENTS

| | | | |
|---|---|---|---|
| 3,985,615 A | 10/1976 | Kubo | |
| 5,728,386 A | 3/1998 | Provost et al. | |
| 6,039,958 A | 3/2000 | Koyama et al. | |
| 6,051,238 A | 4/2000 | Volkin et al. | |
| 6,210,683 B1 | 4/2001 | Burke et al. | |
| 6,258,362 B1 | 7/2001 | Loudon et al. | |
| 6,841,373 B2 | 1/2005 | Metcalfe | |
| 2001/0012516 A1 | 8/2001 | Efstathiou et al. | |
| 2011/0189233 A1 | 8/2011 | Nagaike et al. | |
| 2013/0209506 A1 | 8/2013 | Cohen et al. | |
| 2019/0167784 A1 | 6/2019 | Cohen et al. | |

FOREIGN PATENT DOCUMENTS

| | | |
|---|---|---|
| WO | WO 2004/042031 | 5/2004 |
| WO | WO 2006/012092 | 2/2006 |

OTHER PUBLICATIONS

GenBank Accession CAA27912, single-stranded DNA-binding protein [Human herpesvirus 3 strain Dumas], 2005.*
Accession No. AB097932 (gI 26665420), "Human herpesvirus 3 DNA, complete genome, strain: Oka, sub_strain: vOka".
Accession No. AB097933 (gI 26665422), "Human herpesvirus 3 DNA, complete genome, strain: Oka, sub_strain: pOka".
Genbank database NC_001348 (gI 9625875), "Human herpesvirus 3, complete genome."
Genbank database X04370 (gI 59989; strain Dumas), "Human herpesvirus 3 (strain Dumas) complete genome."
Annunziato et al., "Varicella-zoster virus proteins in skin lesions: implications for a novel role of ORF29p in chickenpox." *J. Virol.* 74:2005-2010 (2000).
Berthomme et al., "Evidence for a Bidirectional Element Located Downstream from the Herpes Simplex Virus Type 1 Latency-Associated Promoter That Increases Its Activity during Latency," *J. Virol.* 74(8):3613-3622 (2000).
Berthomme et al., "Enhancer and Long-Term Expression Functions of Herpes Simplex Virus Type 1 Latency-Associated Promoter are both Located in the Same Region," *J. Virol.*, vol. 75:4386-4393, 2001.
Boucaud et al., "The varicella-zoster virus (VZV) open-reading frame 29 protein acts as a modulator of a late VZV gene promoter." *J. Infect. Dis.* 178 Suppl 1:S34-8 (1998).
Brunell et al., "Viral gene expression in rat trigeminal ganglia following neonatal infection with varicella-zoster virus." *J. Med. Virol.* 58:286-290 (1999).
Bush et al., "Correct intranuclear localization of herpes simplex virus DNA polymerase requires the viral ICP8 DNA-building protein." *J. Virol.* 65

(56) References Cited

OTHER PUBLICATIONS

Cohen et al., "Absence or Overexpression of the Varicella-Zoster Virus (VZV) ORF29 Latency-Associated Protein Impairs Late Gene Expression and Reduces VZV Latency in a Rodent Model," *J. Virol.* 81(4): 1586-1591, 2007.
Cohen et al., "The varicella-zoster virus ORF63 latency-associated protein is critical for establishment of latency." *J. Virol.* 78:11833-11840 (2004).
Cohen et al., "Varicella-zoster virus ORF4 latency-associated protein is important for establishment of latency." *J. Virol.* 79:6969-6975 (2005).
Cohrs et al., "Analysis of individual human trigeminal ganglia for latent herpes simplex virus type 1 and varicella-zoster virus nucleic acids using real-time PCR." *J. Virol.* 74:11464-11471 (2000).
Cohrs et al., "Characterization of varicella-zoster virus gene 21 and 29 proteins in infected cells." *J. Virol.* 76:7228-7238 (2002).
Cohrs et al., "Varicella-zoster virus (VZV) transcription during latency in human ganglia: detection of transcripts mapping to genes 21, 29, 62, and 63 in a cDNA library enriched for VZV RNA." *J. Virol.* 70:2789-2796 (1996).
Condreay et al., "Transient and stable gene expression in mammalian cells transduced with a recombinant baculovirus vector." *Proc Natl Acad Sci USA* 96:127-132 (1999).
Da Costa et al., "Construction and comparison of a replication-defective herpes simplex virus 2 ICP8 mutant strain and its use in immunization studies in a guinea pig model of genital disease." *Virology* 232:1-12 (1997).
Da Costa et al., "Comparison of different forms of herpes simplex replication-defective mutant viruses as vaccines in a mouse model of HSV-2 genital infection." *Virology* 288:256-263 (2001).
Davison A.J., et al., "The complete DNA sequence of varicella-zoster virus." *J. Gen. Virol.* 67:1759-1816 (1986).
Ferrin et al., "Selective cleavage of human DNA: RecA-assisted restriction endonuclease (RARE) cleavage." *Science* 254:1494-1497 (1991).
Gao et al., "Genetic evidence for multiple nuclear functions of the herpes simplex virus ICP8 DNA-binding protein." *J. Virol.* 63-5258-5267 (1989).
Grinfeld et al., "Translation of varicella-zoster genes during human ganglionic latency." *Virus Genes* 29:317-319 (2004).
He et al., "Cis and trans elements regulating expression of the varicella-zoster virus gI gene." *Arch. Virol. Suppl.* 17:57-60 (2001).
Hoover et al., "Downregulation of Varicella-Zoster Virus (VZV) Immediate-Early ORF62 Transcription by VZV ORF63 Correlates with Virus Replication In Vitro and with Latency," *J. Virol.* 80(7): 3459-3469, 2006.
Ito et al., "Promoter Sequences of Varicella-Zoster Virus Glycoprotein I Targeted by Cellular Transactivating Factors Sp1 and USF Determine Virulence in Skin and T Cells in SCIDhu Mice In Vivo," *J. Virol.* 77(1):489-498, 2003.
Jones et al., "Mutational Analysis of the Varicella-Zoster virus ORF62/63 Intergenic Region," *J. Virol.* 80(6):3116-3121, 2006.
Jones et al., "Biological properties of herpes simplex virus 2 replication defective mutant strains in a murine nasal infection model." *Virology* 278:137-150 (2000).
Kennedy et al., "Latent varicella-zoster virus in human dorsal root ganglia." *Virology* 258:451-454 (1999).
Kennedy et al., "Varicella-zoster virus gene expression in latently infected and explanted human ganglia." *J. Virol.* 74:11893-11898 (2000).
Kennedy et al., "Varicella-zoster virus gene expression in latently infected rat dorsal root ganglia." *Virology* 289:218-223 (2000).
Kinchington et al., "Identification and characterization of a varicella-zoster virus DNA-binding protein by using antisera directed against a predicted synthetic oligonucleotide." *J. Virol.* 62:802-809 (1988).
Kinchington et al., "The varicella-zoster virus immediate early protein IE62 is a major component of virus particles." *J. Virol.* 66:359-366 (1992).
Leib et al., "Immediate-early Regulatory Gene Mutants Define Different Stages in the Establishment and Reactivation of Herpes Simplex Virus Latency," *J. Virol.* 63(2): 759-768, 1989.
Lungu et al., "Aberrant intracellular localization of varicella-zoster virus regulatory proteins during latency." *Proc Natl Acad Sci USA* 95:7080-7085 (1998).
Meier et al., "Varicella-zoster virus transcription in human trigeminal ganglia." *Virology* 193:193-200 (1993).
Meier et al., "The cellular transcription factor USF cooperates with varicella-zoster virus immediate-early protein 62 to symmetrically activate a bidirectional viral promoter." *Mol. Cell Biol.* 14(10):6896-6906 (1994).
Meier et al., "Varicella-zoster virus DNA polymerase and major DNA-binding protein genes have overlapping divergent promoters." *J. Virol.* 67:7573-7581 (1993).
Moriuchi et al., "The acidic amino-terminal region of varicella-zoster open reading frame 4 protein is required for transactivation and can functionally replace the corresponding region of herpes simplex virus ICP27." *Virology* 208:376-382 (1995).
Morrison et al., "Immunization with replication-defective mutants of herpes simplex virus type 1: sites of immune intervention in pathogenesis of challenge virus." *J. Virol.* 68:689-696 (1994).
Ng et al., "Phosphorylation of varicella-zoster virus open reading frame (OFR) 62 regulatory product by viral ORF47-associated protein kinase." *J. Virol.* 68:1350-1359 (1994).
Nguyen et al., "Replication-defective mutants of herpes simplex virus (HSV) induce cellular immunity and protect against lethal HSV infection." *J. Virol.* 66:7067-7072 (1992).
Ou et al. "Simian varicella virus gene 28 and 29 promoters share a common upstream stimulatory factor-binding site and are induced by IE62 transactivation," *J. Gen. Virol.* 87(6): 1501-1508, 2006.
Paulson et al., "Methylation of the EBV Genome and Establishment of Restricted Latency in Low-Passage EBV-Infected 293 Epithelial Cells," *Virology* 299(1): 109-121, 2002.
Ruyechan, "The major herpes simplex virus DNA-binding protein holds single-stranded DNA in an extended conformation." *J. Virol.* 46:661-666 (1993).
Sadzot-Delvaux et al., "Varicella-zoster virus latency in the adult rat is a useful model for human latent infection." *Neurology* 45 (Suppl 8):S18-S20 (1995).
Sato et al., "Varicella-zoster virus open reading frame 2 encodes a membrane phosphoprotein that is dispensable for viral replication and for establishment of latency." *J. Virol.* 76:3575-3578 (2002).
Sato et al., "Varicella-zoster virus ORF47 protein kinase which is required for replication in human T cells, and ORF66 protein kinase which is expressed during latency, are dispensable for establishment of latency." *J. Virol.* 77:11180-11185 (2003).
Sharrar et al., "The postmarketing safety profile of varicella vaccine." *Vaccine* 19:916-923 (2000).
Stallings et al., "Dissection of a novel nuclear localization signal in open reading frame 29 of varicella-zoster virus." *J. Virol.* 79:13070-13081 (2005).
Stallings et al., "The cellular localization pattern of varicella-zoster virus ORF29p is influenced by proteosome-mediated degradation." *J. Virol.* 80:1497-1512 (2006).
Webster et al., "The varicella-zoster virus origin-binding protein can substitute for the herpes simplex virus origin-binding protein in a transient origin-dependent DNA replication assay in insect cells." *Virology* 206:655-660 (1995).
Wise et al., "Postlicensure Safety Surveillance for Varicella Vaccine" *JAMA* 284:1271-1279 (2000).
Xia et al., "Varicella-zoster virus ORF21, which is expressed during latency, is essential for virus replication but dispensable for establishment of latency." *J. Virol.* 77:1211-1218 (2003).
Yang et al., "The DNA element controlling expression of the varicella-zoster virus open reading frame 28 and 29 genes consists of two divergent unidirectional promoters which have a common USF site." *J. Virol.* 78:10939-10952 (2004).
Zapata et al., "Engineering linear F(ab')2 fragments for efficient production in Escherichia coli and enhanced antiproliferative activity." *Protein Eng.*, 8:1057-1062 (1995).

(56) References Cited

OTHER PUBLICATIONS

Zhou et al., "Glycoprotein D or J delivered in trans blocks apoptosis in SK-N-SH cells induced by a herpes virus 1 mutant lacking intact genes expressing both glycoproteins." *J. Virol.* 74:11782-11791 (2000).

* cited by examiner

RECOMBINANT VIRUS WITH DIMINISHED LATENCY AND METHODS OF USING SAME

CROSS REFERENCE TO RELATED APPLICATIONS

This is a divisional of U.S. application Ser. No. 16/195,247, filed Nov. 19, 2018, issued as U.S. Pat. No. 11,305,009 on Apr. 19, 2022, which is a divisional of U.S. application Ser. No. 12/514,011, filed Dec. 21, 2012, issued as U.S. Pat. No. 10,166,285 on Jan. 1, 2019, which is the U.S. National Stage of Application No. PCT/US2007/084331, filed Nov. 9, 2007, which claims priority to U.S. Provisional Application No. 60/857,766, filed Nov. 9, 2006. The above-listed applications are herein incorporated by reference in their entirety.

BACKGROUND

Chickenpox is caused by acute infection with varicella-zoster virus (VZV). The virus spreads throughout the body and enters cells of the nervous system. Latent infection occurs and the virus establishes itself in dorsal root and cranial nerve ganglia. The latent virus subsequently can reactivate and present as zoster (shingles). Researchers and pharmaceutical companies have developed chickenpox vaccines but the side effect of shingles due to the live virus establishing a latent infection is still of concern. The ability of a live virus vaccine to enter and maintain a latent infection phase therefore can compromise the safety of live viral vaccines. Any change to the virus that decreases the probability of establishing or maintaining a latent infection can bring significant public health benefits.

Live vaccines are very popular despite the possibility of latent infection. For example, the live attenuated VZV vaccine based on the "Oka virus" (see, U.S. Pat. No. 3,985,615) prevents chickenpox but the virus used in this vaccine can enter a latent infection phase in vaccinated individuals and later cause zoster (Sharrar et al. Vaccine 19:916 (2000), Wise et al. JAMA 284:1271 (2000)) The Oka virus is attenuated. However the reason for this attenuation and its significance to the latency problem is unknown.

During latency of VZV a limited repertoire of viral genes are expressed including open reading frames (ORFs) 4, 21, 29, 62, 63, and 66. ORF29 transcripts have been detected in human and rodent ganglia by in situ hybridization and reverse-transcription followed by PCR. (Cohrs et al, J. Vir. 74:11464(2000); Kennedy et al., Virology 289:218 (2000). ORF29 encodes a 130 kDa protein that binds to single-stranded DNA and localizes predominantly to the nucleus of virus-infected cells in vitro (Kinchington et al, J. Virol. 62:802 (1988)). ORF29 contains a nuclear localization signal within amino acids 9 to 154 and transport to the nucleus requires Ran and karyopherins (Stallings et al., J. Virol. 79:10370 (2005)). While ORF29 protein is present in the nucleus of lytically infected cells, the protein is in the cytoplasm of neurons from human ganglia (Grinfeld et al, virus Genes 29:317 (2004); Lungu et al, PNAS 95:7080 (1998)). ORF29 protein localizes to the cytoplasm of guinea pig enteric ganglia neurons and in an astrocyte-like cell line (Chen et al, J. Med. Virology (Suppl. 1):S71(2003); Stallings et al., J. Virol. 80:1497 (2006)). Treatment with a proteosome inhibitor or expression of HSV-11CPO or VZV ORF61 results in translocation of ORF29 protein to the nucleus in both guinea pig enteric ganglia neurons and the astrocyte-like cell line.

ORF29 protein is secreted from VZV-infected fibroblasts and is endocytosed by human neurons in vitro (Annunziato et al., J. Virology 74:2005 (2000)). The protein is present in endothelial and epithelial cells in the skin of patients with varicella zoster; the protein is also located in nerves in the dermis of patients with varicella. ORF29 protein is not present in virions (Kinchington et al, J. Virology 66:359 (1992)). The relationship of ORF 29 protein and latency has not been established.

Improved vaccines both for humans and for veterinary care, are needed that comprise altered viruses that present less risk of establishing or maintaining a latent infection and therefore are less likely to reactivate.

SUMMARY

The disclosure provides recombinant herpes virus with diminished latency. In embodiments, the recombinant herpes virus comprises a latency gene or transcript linked to a heterologous promoter or a modified promoter. The disclosure also provides compositions and methods for inducing immunity in animals using the recombinant herpes viruses.

In one aspect, a recombinant virus includes all or a portion of a herpes virus genome, wherein the genome has the promoter for a latency gene or transcript altered or modified so that the gene or transcript is expressed during virus replication, but not expressed or poorly expressed during latency. In embodiments, a recombinant virus has the promoter for a latency gene or transcript replaced by a heterologous promoter. In other embodiments, a recombinant virus has a deletion in a latency gene or transcript at its native location, and the latency gene or transcript is located at different location in the viral genome and is expressed from a heterologous promoter. The recombinant virus as described herein can replicate but has an impaired ability to establish latency. In embodiments, the recombinant virus is attenuated.

Any herpes virus can be altered or modified as described herein. In some embodiments, the herpes virus is selected from the group consisting of herpes simplex virus, varicella-zoster virus (VZV), Marek's disease virus, pseudorabies virus, or cytomegalovirus. In other embodiments, the herpes virus is selected from the group consisting of simian varicella virus, feline herpes 1, equine herpes 1, equine herpes 4, pseudorabies virus, canine herpes 1, bovine herpes 1, Marek's disease virus (of chicken), Laryngotracheitis virus, Meleagrid herpes virus 1, and herpes simplex virus.

Genes or transcripts expressed during a latent herpesvirus infection can be identified. In embodiments, the herpes virus is VZV and the latency gene is selected from the group consisting of genes that correspond to ORF4, ORF21, ORF29, ORF62, ORF63, ORF66 of VZV and combinations thereof. In other embodiments, the gene is homologous to a latency gene or transcript, such as VZV ORF29.

In some embodiments, the promoter associated with a latency gene or transcript is modified or altered to provide for expression during replication but is not expressed or poorly expressed during latency. In other embodiments, the latency gene or transcript is linked to a heterologous promoter. In embodiments, the heterologous promoter can be from the same virus, from a different virus, or from a nonviral source.

In some cases, the recombinant virus has a modified latency gene at its native location, wherein all or a portion of the latency gene or flanking sequences thereof are deleted. In an embodiment, a recombinant virus substantially lacks a DNA binding protein encoding gene at its native location, the gene being encoded by a nucleic acid sequence that hybridizes to a nucleic acid sequence that encodes an ORF29 protein of varicella zoster virus. In other embodiments, the nucleic acid encoding the major DNA binding protein has a deletion of a nucleic acid that encodes at least 10 amino acids. For example, a nucleic acid encoding amino acids corresponding to amino acids 22-957 of an ORF29 having the amino acid sequence of SEQ ID NO:3 is deleted.

In embodiments, where the latency gene or transcript is located at a non native location, the latency gene or transcript is located between other genes, especially those not required for replication, so as not disrupt viral replication.

Another aspect of the disclosure provides immunogenic compositions and methods of using immunogenic compositions. As described herein an immunogenic composition includes a recombinant herpesvirus as described herein and a carrier. The immunogenic composition may further include an adjuvant or a live vaccine stabilizer.

The immunogenic compositions are useful in methods of preventing, diminishing herpes viral infection and/or establishment or maintenance of latency.

DETAILED DESCRIPTION

Figure 1:
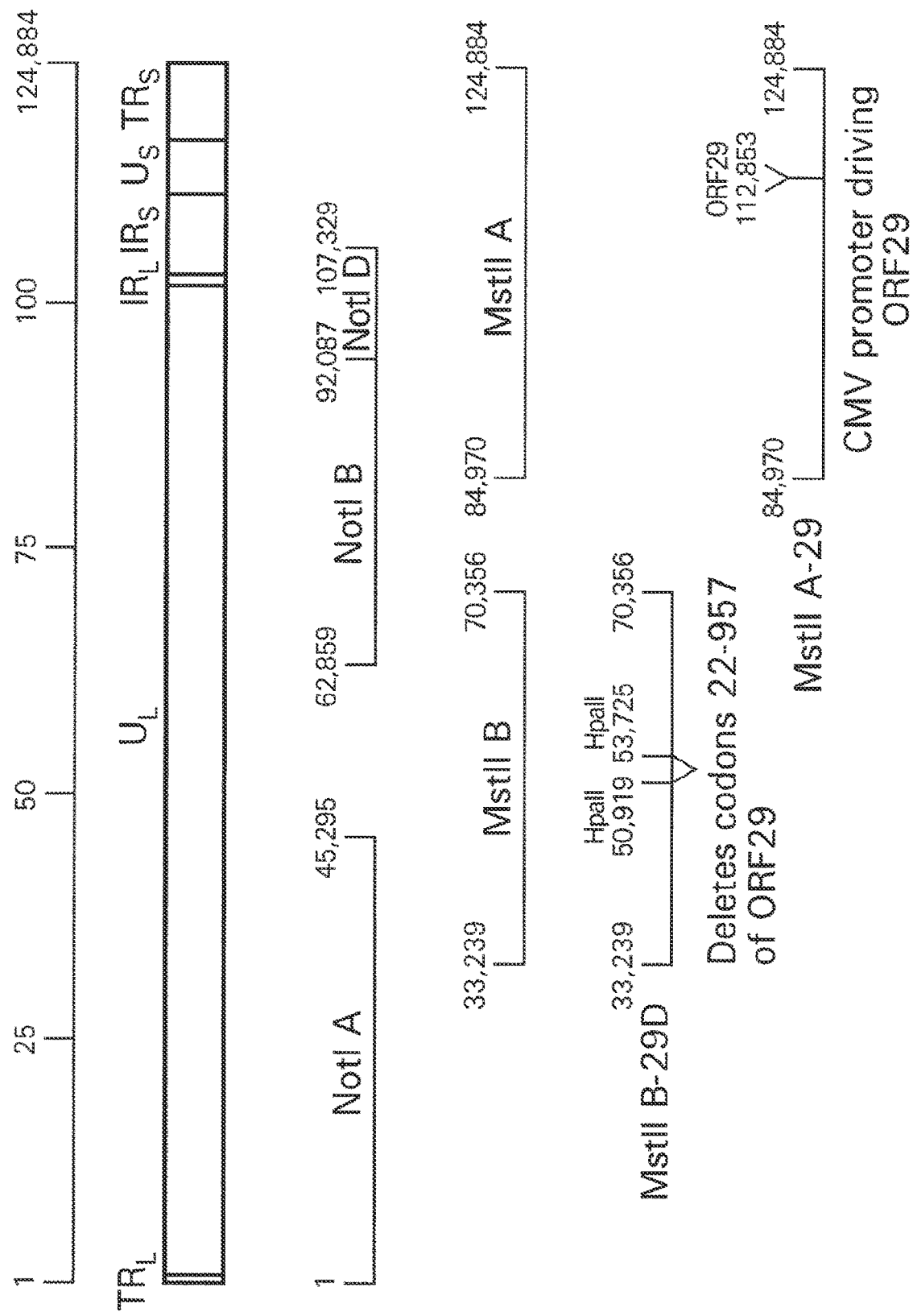
FIG. 1. Construction of recombinant VZV deleted for ORF29 and an ORF29 repaired virus. The VZV genome (line 1) consists of unique long (UL), unique short (US), terminal repeat (TR) and internal repeat (IR) regions (line 2). Cosmids NotI A and NotI B (line 3), MstII A and MstII B (line 4) encompass the VZV genomic. Cosmid MstII B-29D is deleted for most of ORF29 (line 5). Cosmid MstII A-29 has a cassette with ORF29 driven by the human CMV promoter inserted into the AvrII site of the cosmid (line 6). Numbers indicate nucleotide positions based on the sequence of VZV Dumas strain.

The term "attenuated" as used herein refers to a virus that is weakened or impaired for virulence.

The term "antibody" is used in the broadest sense and specifically includes, for example, single monoclonal antibodies, antibody compositions with polyepitopic specificity, single chain antibodies, and fragments of antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., 1995, Protein Eng., 8:1057-1062); single-chain antibody molecules; and multispecific antibodies formed from antibody fragments.

The term "binds specifically" refers to an antibody that binds VZV and does not substantially bind other herpes viruses.

"Carriers" as used herein include pharmaceutically acceptable carriers, excipients, or stabilizers, which are nontoxic to the cell or mammal being exposed thereto at the dosages and concentrations, employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "VZV" as used herein refers to an isolate, strain, or recombinant varicella zoster virus. In embodiments, the genome is about 125-kbp long and includes terminal repeat (TR), unique long (UL)repeat, internal repeat (IR), and unique short repeat (US) DNA domains. VZV can be isolated from infected humans and propagated in cell lines, such as human embryonic lung cells. An attenuated vaccine strain has been described in Gomi et al, Journal of Virology 76:11447 (2002). The complete sequences of VZV Oka strain and vaccine strain have accession nos. AB097932 (gI 26665420) and AB097933 (gI 26665422), respectively. A reference sequence in the Genbank data base is found at NC_001348 (gI 9625875) or X04370 (gI 59989; strain Dumas). Numbering of the nucleotides of the sequences presented herein is in reference to the VZV, strain Dumas as exemplified in X04370.

The term "immunogenic effective amount" of a recombinant virus or component thereof refers to an amount of a recombinant virus or component thereof that induces an immune response in an animal. The immune response may be determined by measuring a T or B cell response. Typically, the induction of an immune response is determined by the detection of antibodies specific for the recombinant virus or component thereof.

An "isolated" antibody is an antibody that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source. Preferably, the isolated nucleic is free of association with all components with which it is naturally associated. An isolated nucleic acid molecule is other than in the form or setting in which it is found in nature.

"Percent (%) nucleic acid sequence identity" with respect to the nucleic acid sequences identified herein is defined as the percentage of nucleotides in a candidate sequence that are identical with the nucleotides in a reference herpesvirus nucleic acid sequence, after aligning the sequences and introducing gaps, if necessary, to achieve the maximum percent sequence identity. In some embodiments, the reference VZV nucleic acid sequence is that of SEQ ID NO:1 or SEQ ID NO:11. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

100 times the fraction W/Z where W is the number of nucleotides scored as identical matches by the sequence alignment program in that program's alignment of A and B. and where Z is the total number of nucleotides in B. It will be appreciated that where the length of nucleic acid sequence A is not equal to the length of nucleic acid sequence B, the % nucleic acid sequence identity of A to B will not equal the % nucleic acid sequence identity of B to A.

"Recombinant" refers to a polynucleotide that has been isolated and/or altered by the hand of man. A DNA sequence encoding all or a portion of a herpesvirus viral genome may be isolated and altered or modified as described herein.

"Percent (%) amino acid sequence identity" with respect to the herpesvirus polypeptide sequences identified herein is defined as the percentage of amino acid residues in a candidate sequence that are identical with the amino acid residues in a herpesvirus polypeptide reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, clustal V (DNASTAR) or Megalign (DNASTAR) software. Those skilled in the art can determine appropriate parameters for measuring alignment, including any algorithms needed to achieve maximal alignment over the full-length of the sequences being compared. Alignments of ORF from different VZV strains, variants and isolates can be determined using sequences known or readily determined by those of skill in the art. A reference sequence for ORF 29 is that of a polypeptide comprising the amino acid sequence of SEQ ID NO:3 or SEQ ID NO:10.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. In an embodiment, the B amino acid sequence is that of SEQ ID NO:3 or SEQ ID NO:10.

"ORF29 polypeptide variant" refers to an ORF29 polypeptide that differs in amino acid sequence from a particular ORF29 polypeptide reference sequence. In an embodiment, the ORF29 polypeptide reference sequence comprises an amino acid sequence of SEQ ID NO:3 or SEQ ID NO:10. The variants may include deletions and additions of amino acids, as well as amino acid substitutions as described herein.

An ORF29 polypeptide variant has at least about any number of % sequence identity from 70% to 100% sequence identity to a full-length mature ORF29 polypeptide reference sequence. An ORF29 variant has at least about 70% sequence identity, more preferably at least about 75% sequence identity, more preferably at least about 80% sequence identity, more preferably at least about 85% sequence identity, more preferably at least about 90% sequence identity, more preferably at least about 95% sequence identity and even 100% sequence identity to an ORF29 polypeptide reference sequence such as that of SEQ ID NO: 3 or SEQ ID NO:10.

An ORF29 polypeptide variant has at least about any amount of % deleted amino acids from 0.2% to 100% of a full-length mature ORF29 polypeptide reference sequence, such as SEQ ID NO:3 or SEQ ID NO:10. An ORF29 variant has at least about 0.2% deleted, more preferably at least about 4% amino acids deleted, more preferably at least about 10%, more preferably at least about 15%, more preferably at least about 20%, and more preferably at least about 25% amino acids deleted.

The disclosure also includes variants of nucleic acid molecules encoding ORF29 polypeptides. In one embodiment, the disclosure includes polynucleotides encoding a polypeptide having at least about any number of sequence identity from 70% to 100/o sequence identity to the reference polypeptide for ORF29, more preferably about 70% sequence identity, more preferably about 75% sequence identity, more preferably about 80% sequence identity, more preferably about 85% sequence identity, more preferably about 90% sequence identity, more preferably about 95% sequence identity, and even up to 100% sequence identity to a reference ORF29, such as that having an amino acid sequence of SEQ ID NO:3 or SEQ ID NO:10. The variants may include deletions and additions of nucleotides, as well as nucleotide substitutions as described herein. A reference sequence for a nucleic acid sequence encoding an ORF29 polypeptide is that comprising sequence of SEQ ID NO:1 or SEQ ID NO:11.

An ORF29 nucleic acid variant has at least about any amount of % deleted nucleotides from 0.2% to 100% of a full-length mature ORF29 nucleic acid reference sequence, such as SEQ ID NO:1 or SEQ ID NO:11. An ORF29 variant has at least about 0.2% deleted, more preferably at least about 4% nucleotides deleted, more preferably at least about 10%, more preferably at least about 15%, more preferably at least about 20%, and more preferably at least about 25% nucleotides deleted.

TABLE 1

| (Nucleic Acid Sequence for ORF29 for VZV from NC_001348; SEQ ID NO: 1) |
|---|
| 50857 atgg aaaatactca gaagactgtg |
| 50881 acagtgccca cggggcccct gggttacgtt tatgcgtgcc gggttgaaga tttggatctg |
| 50941 gaggaaattt catttttggc cgctcgtagc acggactctg atttggcttt attacctttg |
| 51001 atgcgtaatt tgaccgtgga aaaaactttt acatccagcc tggcggtggt ttctggagca |
| 51061 cgcactacgg gtcttgccgg agctggtatt accttaaaac tcactaccag tcatttctat |
| 51121 ccatctgtct ttgtctttca cggaggcaaa cacgttttac ccagctccgc ggccccaaat |
| 51181 ctcacacgcg cgtgtaacgc ggctcgagaa cggtttgggt tttcacgctg ccaagggcct |
| 51241 cctgttgacg gtgctgttga gacgaccggc gctgagatat gcacccgcct tggattagag |
| 51301 ccagaaaata caatattata cttggtggtc acggcattgt ttaaggaagc cgtatttatg |
| 51361 tgcaacgtgt ttctgcatta tggaggactc gatattgttc atattaacca tggggatgtt |
| 51421 atacgtatac cgttatttcc ggtacaactt ttcatgcccg atgttaaccg tctggtaccc |
| 51481 gacccattca acactcatca caggtctatc ggagagggtt ttgtataccc aacacccttt |
| 51541 tataacaccg ggttgtgcca tttaatacat gactgtgtta ttgctcccat ggccgttgcc |
| 51601 ttgcgcgtca gaaatgtaac tgccgtcgcc cgaggagcgg cccaccttgc ttttgatgaa |
| 51661 aatcacgagg gggcagtact ccccccctgac attacgtaca cgtattttca gtcctcttca |
| 51721 agtggaacca ctaccgcccg tggagcgcgt cgaaacgatg tcaactccac gtctaagcct |
| 51781 agcccatcgg gggggtttga aagacggttg gcgtctatta tggccgctga cacagccttg |
| 51841 cacgcagaag ttatattcaa cactggaatt tacgaagaaa ctccaacaga tatcaaagaa |
| 51901 tggccaatgt ttataggcat ggagggcact ttgccaaggc taaacgctct ggggtcatat |
| 51961 accgctcgtg tggccggggt cattggtgcg atggttttca gcccaaattc tgcgttgtat |
| 52021 ctaactgagg tggaggatag cgggatgacc gaagccaagg atgggggacc gggtccatca |
| 52081 tttaatcgat tttaccagtt tgccggacct catttagctg cgaatcccca aacagatcga |
| 52141 gatggccacg ttctatccag tcagtctacg ggttcatcaa acacagagtt tagcgtggat |
| 52201 tatttggcac tcatttgtgg atttggagca cccctgttgg cgcgactgct tttttatcta |
| 52261 gaacgctgtg acgctggtgc gtttacaggg ggtcacgggg atgcgttaaa atatgttacg |
| 52321 gggacctttg actctgaaat tccatgtagt ttatgtgaaa aacacacgcg gccggtatgc |
| 52381 gctcacacaa cagtacaccg acttagacaa cgcatgccgc gatttggaca agccacccgt |
| 52441 caacctattg ggtgtttgg aacaatgaac agccaatata gcgactgcga tcctctagga |
| 52501 aactatgctc catatttaat ccttcgaaaa cccggggatc aaacggaagc agcaaaggca |
| 52561 accatgcagg acacttatag ggctacacta gaacgcttgt ttatcgatct agaacaagag |
| 52621 cgactactgg atcgcggtgc cccatgttct tccgagggac tatcgtctgt cattgtggat |

TABLE 1-continued

```
52681 catccaacgt tcgtcgcat attagacaca ctgcgtgcgc gtatagaaca gacaacaaca
52741 caatttatga aagtgttggt tgagacccgc gattataaga tccgtgaagg attatccgaa
52801 gccacccatt caatggcgtt aacgtttgat ccatactcag gagcattttg tcccattacc
52861 aattttttag ttaaacgaac acacctagcc gtggtacaag acttagcatt aagccaatgt
52921 cattgtgtat tttacggaca gcaagttgag gggcggaact tcgtaacca attccaacct
52981 gttttgcggc ggcgttttgt tgacctgttt aatgggggt ttatatcaac acgctctata
53041 accgtaacat tatctgaagg tcctgtatcc gccccaaatc cgacattggg acaagacgcg
53101 cccgcggggc gtacctttga tggggattta gcgcgcgtaa gcgtggaagt tattcgggat
53161 atacgagtta aaaatagggt cgttttttca ggtaactgta caaatctctc tgaggcagcc
53221 cgggcaaggc ttgtaggcct tgcaagtgcg taccaacgcc aagaaaaaag agtggatatg
53281 ttacacgggg ccctagggtt tttgcttaaa cagtttcacg gcctgttatt tcctcggggt
53341 atgccaccaa acagtaaatc ccccaacccg cagtggtttt ggaccctgtt acaacgcaac
53401 cagatgccgg cagataaact tacacacgaa gagattacca ctattgcagc tgttaaacgg
53461 tttaccgagg aatatgcagc aataaacttt attaatctac ccccaacctg cataggagaa
53521 ttagcccagt tttatatggc aaatcttatt cttaaatact gcgatcattc acagtacctt
53581 ataaatacct taacttctat aattacgggt gccaggcgcc cgcgtgaccc atcatccgtt
53641 ttgcattgga ttcgtaaaga tgtcacgtcc gccgcggaca tagaaaccca agcaaaggcg
53701 cttcttgaaa aaacggaaaa cttaccggaa ttatggacta cggcttttac ttcaactcat
53761 ttagtccgcg cggccatgaa tcaacgtccc atggtcgttt taggaataag cattagtaaa
53821 tatcacggag cggcaggaaa caaccgcgtc tttcaggcag ggaattggag cggtttaaac
53881 gggggtaaaa atgtatgccc gctatttaca tttgatcgca ctcgccgttt tataatagca
53941 tgtcctagag gaggttttat ctgccccgta acaggtccct cgtcgggaaa tcgagaaacc
54001 acccctatccg accaagttcg cggtataatt gtcagtggcg gggccatggt tcaattagcc
54061 atatacgcca cggttgtgcg tgcagtgggc gctcgagcac aacatatggc atttgacgac
54121 tggttaagtc ttacagacga tgagttttta gccagagact ggaggagtt acacgaccag
54181 attatccaaa ccctggaaac gccctggacc gtagaaggcg ctctagaagc agtaaagatt
54241 ctagatgaaa aaacgacagc gggagatggg gaaacccca caaacctagc attaatttt
54301 gattcttgtg aaccaagcca tgacaccaca tctaacgtat taaacatttc agggtcaaac
54361 atttcagggt caactgtccc tggtcttaaa cgacccccg aagatgacga actctttgat
54471 cttagtggta ttcccataaa acatgggaac attacaatgg aaatgattta a
```

TABLE 2

(Nucleic Acid sequence for Deletion Mutant of ORF29 (nucleotides 50919 to 53725 deleted); SEQ ID NO: 2)

```
50857 atgg aaaatactca gaagactgtg acagtgccca ggggcccct gggttacgtt 50911 tatgcgtg 53726 cgaaa ttatggacta cggcttttac ttcaactcat 53761 ttagtccgcg cggccatgaa tcaacgtccc atggtcgttt taggaataag cattagtaaa 53821 tatcacggag cggcaggaaa caaccgcgtc tttcaggcag ggaattggag cggtttaaac 53881 gggggtaaaa atgtatgccc gctatttaca tttgatcgca ctcgccgttt tataatagca
```

TABLE 2-continued

| | |
|---|---|
| 53941 | tgtcctagag gaggttttat ctgccccgta acaggtccct cgtcgggaaa tcgagaaacc |
| 54001 | accctatccg accaagttcg cggtataatt gtcagtggcg gggccatggt tcaattagcc |
| 54061 | atatacgcca cggttgtgcg tgcagtgggc gctcgagcac aacatatggc atttgacgac |
| 54121 | tggttaagtc ttacagacga tgagttttta gccagagact tggaggagtt acacgaccag |
| 54181 | attatccaaa ccctggaaac gccctggacc gtagaaggcg ctctagaagc agtaaagatt |
| 54241 | ctagatgaaa aaacgacagc gggagatggg gaaacccccca caaacctagc atttaatttt |
| 54301 | gattcttgtg aaccaagcca tgacaccaca tctaacgtat taaacatttc agggtcaaac |
| 54361 | atttcagggt caactgtccc tggtcttaaa cgaccccccg aagatgacga actctttgat |
| 54471 | cttaatggta ttcccataaa acatgggaac attacaatgg aaatgattta a |

TABLE 3

| |
|---|
| (Nucleic Acid Sequence for ORF29 for VZV from X04370; SEQ ID NO: 11) |
| 50857 atgg aaaatactca gaagactgtg |
| 50881 acagtgccca cggggccCct gggttacgtt tatgcgtgcc gggttgaaga tttggatctg |
| 50941 gaggaaattt catttttggc cgctcgtagc acggactctg atttggcttt attacctttg |
| 51001 atgcgtaatt tgaccgtgga aaaaactttt acatccagcc tggcggtggt ttctggagca |
| 51061 cgcactacgg gtcttgccgg agctggtatt accttaaaac tcactaccag tcatttctat |
| 51121 ccatctgtct ttgtctttca cggaggcaaa cacgttttac ccagctccgc ggccccaaat |
| 51181 ctcacacgcg cgtgtaacgc ggctcgagaa cggtttgggt tttcacgctg ccaagggcct |
| 51241 cctgttgacg gtgctgttga gacgaccggc gctgagatat gcacccgcct tggattagag |
| 51301 ccagaaaata caatattata cttggtggtc acggcattgt ttaaggaagc cgtatttatg |
| 51361 tgcaacgtgt ttctgcatta tggaggactc gatattgttc atattaacca tggggatgtt |
| 51421 atacgtatac cgttatttcc ggtacaactt ttcatgcccg atgttaaccg tctggtaccc |
| 51481 gacccattca acactcatca caggtctatc ggagagggtt ttgtataccc aacacccttt |
| 51541 tataacaccg ggttgtgcca tttaatacat gactgtgtta ttgctcccat ggccgttgcc |
| 51601 ttgcgcgtca gaaatgtaac tgccgtcgcc cgaggagcgg cccaccttgc ttttgatgaa |
| 51661 aatcacgagg gggcagtact ccccccctgac attacgtaca cgtattttca gtcctcttca |
| 51721 agtggaacca ctaccgcccg tggagcgcgt cgaaacgatg tcaactccac gtctaagcct |
| 51781 agcccatcgg gggggtttga aagacggttg gcgtctatta tggccgctga cacagccttg |
| 51841 cacgcagaag ttatattcaa cactggaatt tacgaagaaa ctccaacaga tatcaaagaa |
| 51901 tggccaatgt ttataggcat ggagggcact ttgccaaggc taaacgctct ggggtcatat |
| 51961 accgctcgtg tggccggggt cattggtgcg atggttttca gcccaaattc tgcgttgtat |
| 52021 ctaactgagg tggaggatag cgggatgacc gaagccaagg atgggggacc gggtccatca |
| 52081 tttaatcgat tttaccagtt taccggacct catttagctg cgaatcccca aacagatcga |
| 52141 gatggccacg ttctatccag tcagtctacg ggttcatcaa acacagagtt tagcgtggat |
| 52201 tatttggcac tcatttgtgg atttggagca cccctgttgg cgcgactgct tttttatcta |
| 52261 gaacgctgtg acgctggtgc gtttacaggg ggtcacgggg atgcgttaaa atatgttacg |
| 52321 gggacctttg actctgaaat tccatgtagt ttatgtgaaa aacacacgcg gccggtatgc |
| 52381 gctcacacaa cagtacaccg acttagacaa cgcatgccgc gatttggaca agccacccgt |
| 52441 caacctattg ggtgtttgg aacaatgaac agccaatata gcgactgcga tcctctagga |

TABLE 3-continued

```
52501 aactatgctc catatttaat ccttcgaaaa cccggggatc aaacggaagc agcaaaggca
52561 accatgcagg acacttatag ggctacacta gaacgcttgt ttatcgatct agaacaagag
52621 cgactactgg atcgcggtgc cccatgttct tccgagggac tatcgtctgt cattgtggat
52681 catccaacgt tcgtcgcat attagacaca ctgcgtgcgc gtatagaaca gacaacaaca
52741 caatttatga aagtgttggt tgagacccgc gattataaga tccgtgaagg attatccgaa
52801 gccacccatt caatggcgtt aacgtttgat ccatactcag gagcattttg tcccattacc
52861 aattttttag ttaaacgaac acacctagcc gtggtacaag acttagcatt aagccaatgt
52921 cattgtgtat tttacggaca gcaagttgag gggcggaact ttcgtaacca attccaacct
52981 gttttgcggc ggcgttttgt tgacctgttt aatgggggt ttatatcaac acgctctata
53041 accgtaacat tatctgaagg tcctgtatcc gccccaaatc cgacattggg acaagacgcg
53101 cccgcgaggc gtacctttga tgaggattta gcgcgcgtaa gcgtggaagt tattcgggat
53161 atacgagtta aaatagggt cgttttttca ggtaactgta caaatctctc tgaggcagcc
53221 cgggcaaggc ttgtaggcct tgcaagtgcg taccaacgcc aagaaaaaag agtggatatg
53281 ttacacgggg ccctaggggtt tttgcttaaa cagtttcacg gcctgttatt tcctcggggt
53341 atgccaccaa acagtaaatc ccccaacccg cagtggtttt ggaccctgtt acaacgcaac
53401 cagatgccgg cagataaact tacacacgaa gagattacca ctattgcagc tgttaaacgg
53461 tttaccgagg aatatgcagc aataaactt attaatctac ccccaacctg cataggagaa
53521 ttagcccagt tttatatggc aaatcttatt cttaaatact gcgatcattc acagtacctt
53581 ataaataccct taacttctat aattacgggt gccaggcgcc cgcgtgaccc atcatccgtt
53641 ttgcattgga ttcgtaaaga tgtcacgtcc gccgcggaca tagaaaccca agcaaaggcg
53701 cttcttgaaa aaacggaaaa cttaccggaa ttatggacta cggcttttac ttcaactcat
53761 ttagtccgcg cggccatgaa tcaacgtccc atggtcgttt taggaataag cattagtaaa
53821 tatcacggag cggcaggaaa caaccgcgtc tttcaggcag ggaattggag cggtttaaac
53881 gggggtaaaa atgtatgccc gctatttaca tttgatcgca ctcgccgttt tataatagca
53941 tgtcctagag gaggttttat ctgccccgta acaggtccct cgtcgggaaa tcgagaaacc
54001 accctatccg accaagttcg cggtataatt gtcagtggcg gggccatggt tcaattagcc
54061 atatacgcca cggttgtgcg tgcagtgggc gctcgagcac aacatatggc atttgacgac
54121 tggttaagtc ttacagacga tgagttttta gccagagact tggaggagtt acacgaccag
54181 attatccaaa ccctggaaac gccctggacc gtagaaggcg ctctagaagc agtaaagatt
54241 ctagatgaaa aaacgacagc gggagatggg gaaaccccca caaacctagc atttaattt
54301 gattcttgtg aaccaagcca tgacaccaca tctaacgtat taaacatttc agggtcaaac
54361 atttcagggt caactgtccc tggtcttaaa cgaccccccg aagatgacga actctttgat
54421 cttagtggta ttcccataaa acatgggaac attacaatgg aaatgattta a
```

TABLE 4

(Amino Acid Sequence for ORF29 for VZV from NC_001348; SEQ ID NO: 3)
MENTQKTVTVPTGPLGYVYACRVEDLDLEEISFLAARSTDSDLA

LLPLMRNLTVEKTFTSSLAVVSGARTTGLAGAGITLKLTTSHFYPSVFVHGGKHVLP

SSAAPNLTRACNAARERFGFSRCQGPPVDGAVETTGAEICTRLGLEFENTILYLVVTA

TABLE 4-continued

LFKEAVFMCNVFLHYGGLDIVHINHGDVIRIPLFPVQLFMPDVNRLVPDPFNTHHRSI

GEGFVYPTPFYNTGLCHLIHDCVIAPMAVALRVRNVTAVARGAAHLAFDENHEGAVLP

PDITYTYFQSSSSGTTTARGARRNDVNSTSKPSPSGGFERRLASIMAADTALHAEVIF

NTGIYEETPTDIKEWPMFIGMEGTLPRLNALGSYTARVAGVIGAMVFSPNSALYLTEV

EDSGMTEAKDGGPGPSFNRFYQFAGPHLAANPQTDRDGHVLSSQSTGSSNTEFSVDYL

ALICGFGAPLLARLLFYLERCDAGAFTGGHGDALKYVTGTFDSEIPCSLCEKHTRPVC

AHTTVHRLRQRMPRFGQATRQPIGVFGTMNSQYSDCDPLGNYAPYLILRKPGDQTEAA

KATMQDTYRATLERLFIDLEQERLLDRGAPCSSEGLSSVIVDHPTFRRILDTLRARIE

QTTTQFMKVLVETRDYKIREGLSEATHSMALTFDPYSGAFCPITNFLVKRTHLAVVQD

LALSQCHCVFYGQQVEGRNFRNQFQPVLRRRFVDLFNGGFISTRSITVTLSEGPVSAP

NPTLGQDAPAGRTFDGDLARVSVEVIRDIRVKNRVVFSGNCTKLSEAARARLVGLASA

YQRQEKRVDMLHGALGFLLKQFHGLLFPRGMPPNSKSPNPQWFWTLLQRNQMPADKLT

HEEITTIAAVKRFTEEYAAINFINLPPTCIGELAQFYMANLILKYCDHSQYLINTLTS

IITGARRPRDPSSVLHWIRKDVTSAADIETQAKALLEKTENLPELWTTAFTSTHLVRA

AMNQRPMVVLGISISKYHGAAGNNRVFQAGNWSGLNGGKNVCPLFTFDRTRRFIIACP

RGGFICPVTGPSSGNRETTLSDQVRGIIVSGGAMVQLAIYATVVRAVGARAQHMAFDD

WLSLTDDEFLARDLEELHDQIIQTLETPWTVEGALEAVKILDEKTTAGDGETPTNLAF

NFDSCEPSHDTTSNVLNISGSNISGSTVPGLKRPPEDDELFDLSGIPIKHGNITMEMI

---

(Ref Amino Acid Sequence for ORF29 for VZV from X04370; SEQ ID NO: 10)

MENTQKTVTVPTGPLGYVYACRVEDLDLEEISFLAARSTDSDLA

LLPLMRNLTVEKTFTSSLAVVSGARTTGLAGAGITLKLTTSHFYPSVFVFHGGKHVLP

SSAAPNLTRACNAARERFGFSRCQGPPVDGAVETTGAEICTRLGLEPENTILYLVVTA

LFKEAVFMCNVFLHYGGLDIVHINHGDVIRIPLFPVQLFMPDVNRLVPDPFNTHHRSI

GEGFVYPTPFYNTGLCHLIHDCVIAPMAVALRVRNVTAVARGAAHLAFDENHEGAVLP

PDITYTYFQSSSSGTTTARGARRNDVNSTSKPSPSGGFERRLASIMAADTALHAEVIF

NTGIYEETPTDIKEWPMFIGMEGTLPRLNALGSYTARVAGVIGAMVFSPNSALYLTEV

EDSGMTEAKDGGPGPSFNRFYQFAGPHLAANPQTDRDGHVLSSQSTGSSNTEFSVDYL

ALICGFGAPLLARLLFYLERCDAGAFTGGHGDALKYVTGTFDSEIPCSLCEKHTRPVC

AHTTVHRLRQRMPRFGQATRQPIGVFGTMNSQYSDCDPLGNYAPYLILRKPGDQTEAA

KATMQDTYRATLERLFIDLEQERLLDRGAPCSSEGLSSVIVDHPTFRRILDTLRARIE

QTTTQFMKVLVETRDYKIREGLSEATHSMALTFDPYSGAFCPITNFLVKRTHLAVVQD

LALSQCHCVFYGQQVEGRNFRNQFQPVLRRRFVDLFNGGFISTRSITVTLSEGPVSAP

NPTLGQDAPAGRTFDGDLARVSVEVIRDIRVKNRVVFSGNCTNLSEAARARLVGLASA

YQRQEKRVDMLHGALGFLLKQFHGLLFPRGMPPNSKSPNPQWFWTLLQRNQMPADKLT

HEEITTIAAVKRFTEEYAAINFINLPPTCIGELAQFYMAMLILKYCDHSQYLINTLTS

IITGARRPRDPSSVLHWIRKDVTSAADIETQAKALLEKTENLPELWTTAFTSTHLVRA

AMNQRPMVVLGISISKYHGAAGNNRVFQAGNWSGLNGGKNVCPLFTFDRTRRFIIACP

RGGFICPVTGPSSGNRETTLSDQVRGIIVSGGAMVQLAIYATVVRAVGARAQHMAFDD

-continued

```
WLSLTDDEFLARDLEELHDQIIQTLETPWTVEGALEAVKILDEKTTAGDGETPTNLAF

NFDSCEPSHDTTSNVLNISGSNISGSTVPGLKRPPEDDELFDLSGIPIKHGNITMEMI"
```

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C. (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrat at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SW (sodium chloride/sodium citrate) and 50% formamide at 55'C, followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, in etc. as necessary to accommodate factors such as probe length and the like.

Recombinant Herpesvirus

The disclosure provides recombinant herpes virus for use in immunogenic compositions and for attenuated live virus compositions. These compositions are useful, interiliac, in a vaccine composition in order to provide immunity against herpesvirus infection while diminishing the establishment or maintenance of latency.

Herpesviridae is the name of a family of enveloped, double-stranded DNA viruses with relatively large complex genomes. They replicate in the nucleus of a wide range of vertebrate hosts, including eight varieties isolated in humans, several each in horses, cattle, mice, pigs, chickens, turtles, lizards, fish, and even in some invertebrates, such as oysters. All herpesvirus virions have four structural elements. The core contains of a single linear molecule of dsDNA in the form of a torus. Surrounding the core is an icosahedral capsid with a 100 nm diameter constructed of 162 capsomeres. Between the capsid and envelope is an amorphous, sometimes asymmetrical, feature named the tegument. It contains viral enzymes, some of which are needed to take control of the cell's chemical processes and subvert them to virion production, some of which defend against the host cell's immediate responses. The envelope is the outer layer of the virion and is composed of altered host membrane and a dozen unique viral glycoproteins.

Herpesvirus genomes range in length from 120 to 230 kbp with base composition from 31% to 75% G+C content and contain 60 to 120 genes. Because replication takes place inside the nucleus, herpesviruses can use both the host's transcription machinery and DNA repair enzymes to support a large genome with complex arrays of genes.

Herpesvirus genes, like the genes of their eukaryotic hosts, are not arranged in operons and in most cases have individual promoters. Essential genes regulate transcription and are needed to construct the virion. Dispensable genes for the most part function to enhance the cellular environment for virus production, to defend the virus from the host immune system and to promote cell to cell spread. All herpesvirus genomes contain lengthy terminal repeats both direct and inverted. Herpes viruses include subfamilies Alphaherpesvirinae. Betaherpesvirinae. and Gammaherpesvirinae.

Members of the subfamily Alphaherpesvirinac are neurotropic (infect nervous system tissue), have a short reproductive cycle (~18 hr.) with efficient cell destruction and variable host range. The human Alphaherpesvirinae with their common name and the disease they cause are: Herpes simplex virus 1; facial, labial and ocular lesions; Herpes simplex virus 2; genital lesions; and Varicella Zoster (Human herpesvirus 3) chicken pox and shingles.

Members of Betaherpesvirinae are lymphotropic, have a long reproductive cycle, restricted host range and infected cells become enlarged (cytomegalo). Human Betaherpesvirinae include: Human cytomegalovirus (Human herpesvirus 5), human herpes virus 6, and human herpesvirus 7.

Gammaherpesvirinae herpesviruses are also lymphotropic and specific for either T or B lymphocytes. Members of this subfamily isolated in humans are: Epstein Barr virus (human herpes 4) and Karposi's sarcoma herpes virus (human herpes 8).

Pseudorabies virus, a non-human pathogen, is an alphaherpesvirus model, both in cell biology and pathogenesis. In addition, the PRV genome provides a close, almost one to one, correspondence of genes to HSV-1, a sexually transmitted infection, and VZV, a common childhood infection causing chicken pox.

It was discovered that modification of a gene encoding a protein expressed during latency or a transcript expressed during latency creates an altered herpesvirus virus that can replicate in vitro but has markedly diminished ability to establish a latent infection. Moreover, immunogenic compositions that contain such modified virus should be safer than regular unmodified live virus vaccines.

In embodiments, the gene or transcript expressed during latency is modified at its native location by altering or replacing the promoter linked with that gene or transcript in the virus. Some herpes viruses may encode latency transcripts which do not encode proteins, such as herpes simplex and pseudorabies virus.

In embodiments, the promoter is altered or replaced with a promoter that is a heterologous promoter, that is, a promoter different from the promoter normally linked to the gene or transcript in the virus. In some embodiments, the promoter is a non latency promoter from the same virus. A latency promoter is a promoter that provides for expression of a gene or transcript that is expressed during latency of a viral infection, in particular, a herpes virus infection. A non latency promoter is any other promoter that can provide for expression of the viral gene or transcript but does not provide for expression of a gene or transcript during latent infection.

The heterologous promoter can be a non latency promoter obtained from the same virus, a promoter (latency or non-latency) from a different herpesvirus or a different virus, or a promoter from a non viral source. In embodiments, the non latency VZV promoter is a promoter from a VZV strain that provides for expression of gene that is not expressed during latency including, but not limited to, VZV ORF10, VZV ORF14, or VZV ORF67. In other embodiments, the promoter is obtained from a gene of a different herpesvirus than the type of herpesvirus being altered and may be a promoter linked to a gene not expressed during latency or expressed during latency. For example, when the virus being altered is VZV, the promoter may be obtained from another herpesvirus, such as a cytomegalovirus (CMV). In other embodiments, the promoter is obtained from a gene from a virus that is not a herpesvirus. Suitable promoters include, without limitation, CMV IE promoter, Herpes simplex virus ICP4 protein promoter, and SV40 early promoter. In embodiments, the promoter is the human CMV IE promoter.

In other embodiments, the native promoter linked with the latency gene or latency transcript in the virus can be altered to provide for expression of the gene or transcript during replication but reduced or no expression during latency. The sequences of promoters associated with latency genes or latency transcripts of herpesviruses are known to those of skill in the art and may be available in publicly available databases such as the eukaryotic promoter database. Alterations to the sequence of a promoter can be made and the altered virus can then be introduced into a host cell or animal to determine the effect of the alteration on viral replication and on expression during latency. Methods for detecting viral replication and expression of viral transcripts during latency are described herein and are known to those of skill in the art.

Some genes or transcripts that are expressed during latency of a herpes virus infection are known to those of skill in the art and include ORFs 4, 21, 29, 62, 63, and 66 of VZV. Genes or transcripts of other herpes virus expressed during latency are known to those of skill in the art and are readily identifiable. A reference describing the genes of herpesvirus is Fields Virology Knipe D M, Howley P M, et al. Philadelphia, Lipincott, Williams & Wilkins, 2007.

Genes that encode latent proteins of VZV, include ORF4, 21, 29, 62, 63, and 66. Exemplary protein and nucleic acid sequences for these genes and the flanking sequences are known to those of skill in the art and are readily identifiable. For example, sequences for ORF4 post transcriptional regulation of gene expression factor protein are described at CAA27887; P09269 (gI 59993); for ORF21 tegument protein are described at CAA27912; P09277 (gI 60010); for ORF 29 major single stranded DNA binding protein are described at CAA27912; P09246 (gI 60018); for ORF62 transcription regulator are described at CAA27945; P09310 (gI60051); for ORF63 host range factor are described at CAA27946; P09255 (gI 60052); and for ORF66 serine threonine protein kinase are described at CAA27949; P09251 (gI60055).

Sequences of the genomes of other herpes viruses and of genes or transcripts expressed during latency are known and can be identified in publicly available databases. The sequences of viral (non latency and latency) promoters and other heterologous promoters are known to those of skill in the art and can be obtained from the eukaryotic promoter database at epd.isb-sib.ch/epd.; or readily determined from nucleic acid sequence using available tools such as the local alignment promoter predictor tool (LAPP).

In embodiments, the latency gene is homologous to the varicella zoster virus and is found in simian varicella virus, feline herpes 1, equine herpes 1, equine herpes 4, pseudorabies virus, canine herpes 1, bovine herpes 1, Marek's disease virus (of chickens), Laryngotracheitis virus, Meleagrid herpes virus 1, or herpes simplex virus. Each such gene can be identified as having sequence similarity to the latency gene, such as the ORF29, of varicella zoster virus and are particularly contemplated for embodiments. Examples of the sequences homologous to ORF29 of varicella zoster virus are shown in Table 6. Examples of sequences of other genes or transcripts expressed during latent infection can be obtained from publicly available data bases in a similar manner.

In some embodiments, the latency gene is a nucleic acid encoding the major DNA binding protein. In an embodiment, the nucleic acid encoding the major DNA binding protein is modified at its native location in the viral genome by replacing the native promoter with a heterologous promoter. In embodiments, the heterologous promoter is another viral promoter and is nonlatency promoter. Sequences of the major DNA binding protein of herpes viruses are available as described in the table below.

TABLE 6

| Protein Sequence | Accession No. | conserved region 1 | conserved region 2 | conserved region 3 | virus subfamily | virus name | gene name |
|---|---|---|---|---|---|---|---|
| gi_10180734 | Q9E6P0; AF243438 | 13-546 | 970-1009 | 606-916 | Alpha | gallid herpesvirus 2/ Marek's disease | UL29 single stranded DNA binding protein-like |
| gi_7673140 | Q9IBU6; AF147806 | 13-545 | 970-1009 | 605-916 | Alpha | gallid herpesvirus 2/ Marek's disease | UL29 |
| gi_5689301 | Q9QTB9; AB024414 | 12-545 | 969-1008 | 605-916 | Alpha | gallid herpesvirus 2/ Marek's disease | UL 29 product homolog |
| gi_5821284 | Q9PZ52; AB024711 | 12-545 | 969-1008 | 605-916 | Alpha | gallid herpesvirus 2/ Marek's disease | homolog of HSV-1 glycoprotein |
| gi_11095862 | Q9E1G3; AF282130 | 13-545 | 969-1008 | 605-916 | Alpha | maleagrid herpesvirus 1 | UL29 major DNA binding protein |
| gi_12025141 | Q9DPQ8; AF291866 | 13-545 | 969-1008 | 605-916 | Alpha | maleagrid herpesvirus 1 | UL29 single stranded DNA binding protein |
| gi_11036573 | Q9E1Y7; AF275348 | 13-540 | 965-1004 | 602-910 | Alpha | cercopithecine herpesvirus 7 | ssDNA binding protein |

TABLE 6-continued

| Protein Sequence | Accession No. | conserved region 1 | conserved region 2 | conserved region 3 | virus subfamily | virus name | gene name |
|---|---|---|---|---|---|---|---|
| gi_60018 | P09246; X04370 | 13-545 | 970-1009 | 607-916 | Alpha | human herpesvirus 3/ varicella-zoster | Unk |
| gi_1150923 | Q89549; X94677 | 13-550 | 978-1017 | 610-920 | Alpha | bovine herpesvirus 1 | major DNA binding protein |
| gi_2605975 | O39273; AF030027 | 13-551 | 978-1017 | 592-900 | Alpha | equid herpesvirus 4 | 31 |
| gi_330823 | P28932; M86664 | 13-551 | 974-1013 | 615-924 | Alpha | equid herpesvirus 1 | single stranded DNA binding protein |
| gi_3721984 | O92611; U80909 | 13-543 | 952-991 | 615-924 | Alpha | pseudorabies virus | DBP |
| gi_1869852 | P89452; Z86099 | 16-547 | 969-1008 | 608-918 | Alpha | human herpesvirus 2/ simplex 2 | Unk |
| gi_535785 | Q69101; D10658 | 16-547 | 969-1008 | 608-918 | Alpha | human herpesvirus 2/ simplex 2 | DNA binding protein ICP8 |
| gi_330121 | P17470; M20165 | 16-547 | 969-1008 | 608-918 | Alpha | human herpesvirus 1/ simplex 1 | ICP8 |
| gi_59529 | P04296; X14112 | 16-547 | 969-1008 | 608-918 | Alpha | human herpesvirus 1/ simplex 1 | Unk |
| gi_5918970 | Q9QH63; AF168792 | 22-554 | 789-828 | 569-867 | Alpha | gallid herpesvirus 1 | DNA binding protein |
| gi_1139643 | P52339; U43400 | 14-512 | 1011-1050 | 569-867 | Beta | human herpesvirus 7 | major DNA binding protein |
| gi_2746271 | O56282; AF037218 | 14-512 | 950-989 | 569-868 | Beta | human herpesvirus 7 | single-strandedd DNA-binding protein |
| gi_405159 | P52538; AF157706 | 14-512 | 976-1015 | 569-868 | Beta | human herpesvirus 6 | U41 |
| gi_854020 | P52338; X83413 | 14-512 | 959-998 | 660-958 | Beta | human herpesvirus 6 | U41, major DNA binding protein |
| gi_1780835 | P17147; X17403 | 13-520 | 938-977 | 600-897 | Beta | human herpesvirus 5/ cytomegalovirus | Unk |
| gi_19881087 | Q8QS31; AF480884 | 13-518 | 957-996 | 625-923 | Beta | chimpanzee cytomegalovirus | single-stranded DNA-binding protein UL57 |
| gi_221811 | P13215; D00750 | 13-518 | 910-949 | 608-906 | Beta | simian cytomegalovirus | Dbp |
| gi_5381306 | Q9WRL7 | 12-522 | 908-947 | 587-885 | Beta | tupaiid herpesvirus | DNBI |
| gi_60535 | P30672; X67021 | 13-521 | 907-946 | 605-904 | Beta | murine cytomegalovirus 1 | major DNA binding protein (MDBP) |
| gi_1255111 | Q85425; AF232689 | 13-371 416-557 | 907-946 | 561-864 | Beta | murine herpesvirus 2/ rat cytomegalovirus | pR57 |
| gi_12802533 | Q99D22; AF318573 | 22-508 | 903-942 | 554-857 | Gamma | bovine herpesvirus 4 | single-stranded DNA-binding protein MDBP |
| gi_1718254 | P88904; U75698 | 20-504 | 903-942 | 554-857 | Gamma | human herpesvirus 8/ Kaposi's sarcoma | Unk |
| gi_2246478 | O40913; U93872 | 20-504 | 912-951 | 558-861 | Gamma | human herpesvirus 8/ Kaposi's sarcoma | Unk |
| gi_4494911 | Q9WRU1; AF083501 | 22-505 | 888-927 | 558-861 | Gamma | Macaca mulatta rhadinovirus 17577 | ssDNA binding protein |
| gi_4019233 | Q9YTQ7; AF083424 | 20-501 | 888-927 | 559-862 | Gamma | ateline herpesvirus 3 | major ssDNA binding protein |
| gi_60327 | P24910 X64346 | 20-501 | 901-940 | 563-866 | Gamma | saimiriine herpesvirus 2 | major ssDNA- binding protein |
| gi_695178 | Q66611; X64346 | 22-509 | 905-944 | 558-861 | Gamma | equid herpesvirus 2 | single-stranded DNA binding protein |
| gi_2045380 | AF478169 | 22-501 | 903-942 | 561-864 | Gamma | porcine lymphotropic herpesvirus 1 | major DNA binding protein |
| gi_2337973 | O36360; AF005370 | 22-503 | 907-946 | 554-855 | Gamma | alcelaphine herpesvirus 1 | major ss DNA binding protein |
| gi_1334916 | P03227; V01555 | 18-501 | 910-949 | 558-859 | Gamma | human herpesvirus 4/ Epstein-Barr | Unk |
| gi_18025535 | Q8UZD2; AY037858 | 18-505 | 920-958 | 555-856 | Gamma | cercopithicine herpesvirus 15 | BALF2 |
| gi_13676643 | Q993K9; AF319782 | 18-502 | 920-958 | 544-842 | Gamma | cercopithicine herpesvirus 3 | ORF2 |
| gi_13249148 | Q992Z6; AF324455 | 13-494 | 921-959 | 544-842 | Gamma | murid herpesvirus 4/ murine herpesvirus 68 | 6 |
| gi_2317927 | O41928; U97553 | 19-494 | 921-959 | 615-691 | Gamma | murid herpesvirus 4/ murine herpesvirus 68 | ssDNA binding protein |

In a desirable embodiment, the latency gene or latency transcript is selected by examination of homology with a conserved region of a variella zoster virus RF29 gene product. Advantageously, the region is at least 10%, 25%, 27%, 28%, 40%, 45%, 50%, 60%, 70%, 80%, 90% or at least 100% identical to the conserved region of the compared gene product. For example corresponding major DNA binding proteins of HSV 1, HSV-2, and pseudorabies virus have about 50% overall amino acid sequence identity, and about the same sequence identity in the DNA binding domain. In addition, such genes or nucleic acids can be identified by hybridization to a nucleic acid sequence encoding an ORF29 protein such as that of SEQ ID NO:1 or SEQ ID NO: 10 under stringent or moderately stringent conditions as described herein.

In embodiments, the DNA binding protein gene is homologous to the varicella zoster virus ORF29 gene or protein and is found in simian varicella virus, feline herpes 1, equine herpes 1, equine herpes 4, pseudorabies virus, canine herpes 1, bovine herpes 1, Marek's disease virus (of chickens), Laryngotracheitis virus, Meleagrid herpes virus 1, or herpes simplex virus. Examples of the sequences homologous to ORF29 of varicella zoster virus arm shown in Table 6.

In some embodiments, the nucleic acid encoding the DNA binding protein linked to the heterologous promoter, located at the native location, has one or more modifications. In some embodiments, the modifications include one or more substitutions or deletions of nucleic acid sequence encoding the nuclear localization signal. For example, in VZV the nuclear localization signal is located at about amino acids 9 to 154. In some embodiments, substitutions or deletions are selected that diminish translocation of the protein to the nucleus. Some deletions of the DNA binding protein include deletions of amino acids 1 to 345; deletion of amino acids 1 to 155, deletion of amino acids 1 to 9; and deletion of amino acids 9 to 154. Substitutions at amino acid positions include positions A35P, F58I, A63V, V93A, S104P, L109H, F122L, G146A, C142R, C169Y, H182Y, C236S and combinations thereof.

In some embodiments, all or a portion of the nucleic acid encoding the gene or transcript expressed during latent infection in its native location is deleted and a nucleic acid encoding the latency protein or comprising the latency transcript is relocated or moved in the viral genome to another location. In embodiments, the latency gene or latency transcript located in the new location is under control of or linked to a heterologous promoter. In other embodiments, the latency gene or transcript located in the new location is linked to its native promoter that has been altered to provide for expression during viral replication but diminished expression during latency.

In embodiments, a nucleic acid encoding a gene or transcript expressed during a latent infection is located in the genome of the recombinant virus at a position different from that of the native location. The native location is the location of the gene or transcript found in the viral genome before any alterations or modification are made in the viral genome or by reference to a reference virus of the same type of virus. The native locations of genes or transcripts involved in latency can readily be determined by reference to the genomic sequences of herpes viruses that are publicly available.

For example, the native location of a gene expressed during latency of VZV can be determined based on a reference virus, such as VZV, strain Dumas. In embodiments, ORF29 in a reference VZV is located at nucleotides 50857 to 54471 of the viral genome of VZV (numbering corresponding to VZV strain Dumas: SEQ ID NO:10). The location of genes encoding major DNA binding proteins of other herpes viruses is readily determined by referring to the viral genome sequences available in publicly available databases, and or by alignment with a reference sequence as described in Table 6.

The genome of herpes viruses is large so that the gene encoding the DNA binding protein may be located at any other location different than the native location but preferably between other known coding sequences that do not interfere with gene expression of the adjacent sequences or do not interfere with sequences important for virus replication. In some embodiments, the gene encoding the DNA binding protein is located in a region of the genome that has restriction sites that provide for ease of insertion of the sequence. In some embodiments, the gene is inserted between ORF 65 and ORF 66 of VZV.

It is desirable for the nucleic acid encoding a gene or transcript expressed during latency, located at a non native location, to be under the control of or linked to a heterologous promoter. As discussed above, in some embodiments, the heterologous promoter is from the same virus, another virus, or a nonviral source. Suitable heterologous promoters include, without limitation, CMV IE promoter, Herpes simplex virus ICP4 protein promoter, and SV40 early promoter. In embodiments, the promoter is the human CMV IE promoter.

In addition, to heterologous promoters, other transcriptional or translational control elements may be incorporated in the nucleic acid. Other regulatory elements, such as termination signals may also optionally be included, such as the SV 40 polyadenylation signal.

It was also discovered that modification, particularly by deletion, of all or a portion of a gene encoding a protein or a transcript expressed during latency, creates an altered virus that can replicate in vitro but has markedly diminished ability to establish a latent infection. In embodiments, the virus is modified both by the presence of a gene encoding a protein or transcript expressed during latency at a non native location linked to a heterologous promoter, and by modification, particularly by deletion, of all or part of the same gene or flanking sequence of the same gene at its native location in the virus.

In some embodiments, substantially all (at least 1%, 10%, 20%, 30%, 40%, 50%, 75%, 85%, 90% or 100% and particularly at least 25%) of the protein coding sequence of all copies of the gene encoding a protein expressed during latency at the native location used in the virus or virus vaccine is deleted. Desirably, the amount of the gene or transcript to be deleted is enough to diminish the function of the protein encoded by the gene or transcript while still providing for expression of a protein (in the case of a gene) that may stimulate an immune response. In other embodiments, the flanking regions of the gene are modified to decrease expression levels during latency. In some embodiments, the latency promoter is deleted or modified.

With respect to VZV ORF29, embodiments include a deletion of at least a nucleic acid encoding at least 10 amino acids. In an embodiment, codons 22 to 957 of the coding sequence of the nucleic acid sequence, such as SEQ ID NO:1 or SEQ ID NO:11 are deleted. Other embodiments, include a deletion of nucleic acids encoding the nuclear localization signal. In VZV ORF29, the nuclear localization signal is at about amino acids 9 to 154.

The recombinant virus with a latency gene or latency transcript linked to an altered or heterologous promoter, the recombinant virus with a latency gene or latency transcript linked to a altered or heterologous promoter at a non native location, and/or the recombinant virus with a latency gene or latency transcript linked to an altered or heterologous promoter at a non native location and that has a deletion of all or part of the latency gene or latency transcript at the native location, has certain properties.

In some embodiments, the recombinant virus has reduced capability to produce proteins expressed late in infection, such as glycoprotein E. Glycoprotein E functions as a low affinity receptor for antibody aggregates and is expressed late during the infection. In embodiments, the recombinant virus has little or no effect on the expression of early and/or intermediate early gene expression of genes, such as IE62, IE63, IE4, viral thymidine kinase, and combinations thereof. In contrast, a gene expressed late in infection such as glycoprotein E is reduced at least 2 fold. The expression of proteins during infection can be determined by methods known to those of skill in the art including a western blot. In embodiments of the recombinant virus described herein, it is desirable to maintain expression and replication of the virus at least to some extent in order to stimulate an immune response when administered to a subject.

In embodiments, a recombinant virus as described herein, has an increased capacity to produce ORF29. In embodiments, a recombinant virus produces at least 1.5 fold to 5 fold more of ORF29 in cell culture.

In embodiments, the recombinant virus can infect dorsal root ganglia during an acute infection. The presence of VZV DNA in dorsal root ganglia of an animal infected with recombinant or wild type virus can be determined using methods known to those of skill in the art, including PCR as described herein.

In embodiments, the recombinant virus has markedly diminished ability to establish a latent infection but is able to replicate. In some cases, the recombinant virus can replicate to a level sufficient to establish an acute infection. Desirably, the recombinant virus can replicate to an amount that is within a log or half a log of the amount of replication of the unaltered virus or a reference virus. In other embodiments, the recombinant virus replicates to an amount comparable to the replication of the virus when unaltered or comparable to a reference virus. In embodiments, a recombinant virus has a decreased ability to cause a latent infection as measured by the presence of nucleic acid known to be associated with latency of herpes viruses, such as ORF63. In some embodiments, latency is impaired by at least 50% as compared to a wild type virus or vaccine strain virus, such as Oka.

Exemplary methods for making recombinant viruses are described herein and are known to those of skill in the art.

Recombinant Herpesvirus/Other Sequences

In an embodiment when one or more deletions are made, one or more protein antigen encoding genetic sequences are added in that location. In a related embodiment a selected viral gene is at least partly deleted and replaced with sequence(s) that encodes one or more epitopes of another viral protein. A viral protein that is synthesized to a high level and that is packaged into the virus, is particularly desired for this embodiment. For example, enough of a protein that forms a viral capsid (or envelope glycoprotein) may be added in place of the deleted portion in-frame with a promoter and initiation codon to allow expression. A skilled artisan may engineer or select a protein that becomes packaged in the regular capsid (or viral envelope). In a related embodiment, a promoter or other regulatory sequence is chosen to allow low enough expression as to avoid formation of unstable virus structures.

In yet another embodiment, a cytokine gene is inserted into the site of deletion of a viral genome or even elsewhere in the genome of the recombinant virus to improve the immunogenicity of the virus. Such replacement and the effects on immunogenicity are known and readily carried out. Advantageously one or more cytokine genes replace one or more deletions of a virus used to make a live virus vaccine.

Immunogenic Compositions and Methods of Use

Another aspect of the disclosure provides immunogenic compositions comprising the recombinant herpesviruses as described herein. In embodiments, the composition comprises a live attenuated recombinant virus having a diminished ability to establish latency, such as, a recombinant virus having a latency gene or latency transcript linked to an altered or heterologous promoter. In other embodiments, a recombinant virus has a latency gene or latency transcript linked to an altered or heterologous promoter at a non native location, and/or a recombinant virus has a latency gene or latency transcript linked to an altered or heterologous promoter at a non native location and has a deletion of all or part of the latency gene or latency transcript at the native location. In embodiments, the composition comprises an adjuvant or a live virus vaccine stabilizer. Other attenuated live herpes virus vaccines may also form part of the composition.

In some embodiments, the immunogenic compositions of the invention comprise an immunogenic effective amount of the recombinant live virus as described herein. An immunogenic effective amount is an amount of live virus that induces an immune response when administered to a host, for example an animal. In embodiments, the composition includes attenuated live recombinant virus that can replicate to an amount that is within one log or 0.5 log of the amount of viral replication of the wild type or a reference virus. The amount of virus in a live attenuated virus vaccine composition can readily be determined based on known vaccine compositions.

The actual amount of the immunogenic composition may vary depending on the animal to be immunized, the route of administration and adjuvants. Immunogenic dosages can be determined by those of skill in the art. The immune response can be humoral, cellular, or both. Generally, the immune response inhibits the herpesvirus viral levels in the immunized host compared to herpesvirus levels in non-immunized hosts. The immunogenic composition optionally includes a pharmaceutically acceptable excipient or carrier.

An embodiment provides an immunogenic composition according to the present disclosure also including immunomodulators such as cytokines or chemokines. In some embodiments, the recombinant virus encodes the immunomodulator or adjuvant. Immunomodulators refers to substances that potentiate an immune response including, but not limited to cytokines and chemokines. Examples of cytokines include but are not limited to IL-2. IL-15, IL-12, or GM-CSF.

An embodiment provides an immunogenic composition further comprising an adjuvant. Such adjuvants may include ganglioside receptor-binding toxins (cholera toxin, LT enterotoxin, their B subunits and mutants); surface immunoglobulin binding complex CTA1-DD; TLR4 binding lipopolysaccharide; TLR2-binding muramyl dipeptide; mannose receptor-binding mannan; dectin-1-binding ss 1,3/1,6 glucans; TLR9-binding CpG-oligodeoxynucleotides; cytokines and chemokines; antigen-presenting cell targeting ISCOMATRIX and ISCOM. Adjuvants such as lipids (fatty acids, phospholipids, Freund's incomplete adjuvant in particular), Vaxfectin, polaxomer, anionic copolymers, CpG units, etc. may be added to the composition. In some embodiments, the adjuvant may be encoded or expressed by the recombinant virus used herein.

An important factor in vaccine formulation is the stabilizer, as vaccine potency may be adversely affected by concentration and storage conditions. Stabilizers often used for live vaccines of viruses such of measles, rubella and mumps generally include one or more saccharides, amino acids, sugar alcohols, gelatin and gelatin derivatives, to stabilize the virus and, in many cases keep the virus from denaturing during a concentration step. In an advantageous embodiment a recombinant virus described herein may by formulated into a vaccine using a stabilizer or other additive that includes native or recombinant serum albumin for this purpose. U.S. Pat. No. 6,210,683 provides representative conditions for this embodiment of the invention. U.S. Pat. Nos. 5,728,386, 6,051,238, 6,039,958 and 6,258,362 also contain details for stabilizers and methods for more gentle treatment of live virus vaccines. Each of these disclosures, and particularly those portions that describe stabilizer compositions and stabilizing methods are specifically incorporated by reference in their entireties.

Another aspect of the disclosure provides for a method for producing a live recombinant virus in amounts sufficient for a vaccine composition. A method for making an attenuated live virus having impaired ability to establish latency, comprises introducing the recombinant virus as described herein into a host cell to produce an amount of the recombinant virus suitable for a vaccine; and recovering the recombinant virus. Suitable host cells for production of the recombinant virus as described herein include human diploid cells, such as MRC5 cells, or Vero cells.

Generally, preparation of a stabilized live virus vaccine begins with centrifugation of a cell culture extract, to obtain a more purified virus fraction. Generally a vaccine stabilizer is then added to the virus fraction, and the mixture diluted. The final desired virus concentration typically will be about 10 to 100,000 PFU (plaque-forming units) and more typically 100 to 10,000 PFU or more of virus content per dose of the stabilized live vaccine. Aliquots of the thus prepared live vaccine may be tested for safety, effectiveness and homogeneity, to confirm eligibility as a vaccine.

After preparation with a stabilizer, the vaccine may be, for example, stored as a lyophilized vaccine, a lyophilized mixed vaccine, a liquid vaccine or a liquid mixed vaccine. Methods for forming these are known. Typically, a lyophilized vaccine is prepared by lyophilizing the vaccine in a vial or an ampule having a volume of about 3 to 30 ml, tightly sealing and storing at a temperature of 5 degrees Centigrade or less. The stored preparation vaccine typically is used according to instructions attached thereto, as a product insert or a notice on the vial or other container. In many cases, a lyophilized vaccine is re-constituted by addition of sterile distilled water before use, and the resultant solution is inoculated by hypodermic injection in an amount, for example, of 0.5 ml per dose. In another embodiment, the vaccine is provided orally.

In an embodiment a modified virus prepared as described herein might be less stable than the wild type from which the virus is derived and a more gentle stabilizer is used. For example, a modified virus that contains one or more added genes that encode other antigens may have a larger amount of genetic material than usual and may be more sensitive to denaturation. In one related embodiment the free divalent cation concentration of the stabilizer or final vaccine formulation is reduced, for example, by the addition of EDTA to counteract this instability. U.S. Pat. No. 6,039,958 for example provides instructions for lowering the concentration of calcium and magnesium in preparations of live virus vaccines. Other techniques described in the literature that alleviate instability and/or facilitate combinations of multiple viruses in the same formulation may of course be used and are contemplated.

The immunogenic compositions of the invention can be in the form of sterile injectable preparations, such as sterile injectable aqueous or oleagenous suspensions. For administration as injectable solutions or suspensions, the immunogenic compositions can be formulated according to techniques well-known in the art, using suitable dispersing or wetting and suspending agents, such as sterile oils, including synthetic mono- or diglycerides, and fatty acids, including oleic acid.

The present disclosure is also directed to uses and methods for immunizing an animal, including a human, other mammals and birds, with the immunogenic compositions of the disclosure to inhibit, control, or prevent herpes virus infection, to inhibit or reduce establishment or maintenance of latency, and/or to inhibit, control, or prevent reactivation of the virus and establishment of a latent infection. Methods for measuring viral replication and for determining the presence of a latent infection are known to those of skill in the art and are described herein. Animals include humans, cats, cows, monkeys, mice, chickens, turkeys, horses, and pigs.

In an embodiment, an animal is immunized with an immunogenic composition of the invention and then boosted one or more times with the immunogenic composition. In an embodiment, the animal is boosted about 2 to about 4 weeks after the initial administration of the immunogenic composition. If the animal is to be boosted more than once, there is about a 2 to 12 week interval between boosts. In an embodiment, the animal is boosted at about 12 weeks and about 36 weeks after the initial administration of the immunogenic composition. The dose used to boost the immune response can include one more cytokines, chemokines, or immunomodulators not present in the priming dose of the immunogenic composition.

The immunogenic compositions of the invention can be administered by intramuscular (i.m.), subcutaneous (s.c.), or intrapulmonary route in dosage unit formulations containing conventional non-toxic pharmaceutically acceptable carriers, adjuvants, or vehicles. Other suitable routes of administration include, but are not limited to intratrachial, transdermal, intraocular, intranasal, inhalation, intracavity, and intravenous (i.v.) administration. Transdermal delivery includes, but is not limited to intradermal, transdermal, and transmucosal administration. Intracavity administration includes, but is not limited to administration into oral or nasal cavities. The immunogenic compositions can be coated onto particles or nanofibers for delivery or formulated in liposomes.

The following examples are provided for illustrative purposes only, and are in no way intended to limit the scope of the present disclosure.

EXAMPLES

Materials and Methods

Cells and viruses. VZV was propagated in human melanoma (MeWo) cells. Recombinant VZV was constructed using cosmids derived from the Oka vaccine strain. The herpes simplex virus type 1 (HSV-1) ICP8 deletion mutant 301 and V827 Vero cells that express HSV-1 ICP8 and ICP27 proteins were gifts from David Knipe. (Gao, M. J. et al., Virol. 63:5258-5267; Da Costa et al., 2001, Virology 288:256-63).

Baculovirus was grown in Sf9 (*Spodoptera fhigiperda*) insect cells using TNM-FH media (PharMingen, San Diego, Calif.). Baculoviruses expressing ORF29 were constructed by cotransfecting Sf9 cells with BaculoGo Id-linearized baculovirus DNA (PharMingen) and either plasmid pAc-CMV29StuI or pAc-CMV 29EcoRV to produce viruses Baculo 29 and Baculo 29EcoRV, respectively. The recombinant baculoviruses were plaque purified on Sf9 cells, concentrated by centrifugation at 8.800×g for 2 hr, and resuspended in phosphate-buffered saline with 1% fetal bovine serum.

Plasmids and cosmids. Plasmid pCI-29 was constructed by performing PCR on VZV cosmid MstII B with primers GCCTAGCTAGCCAAAATGGAAAATACTCAGAA-GACTGTG (SEQ. ID NO:4) and GTCAGAATGCGGCCGCGGGAGGTTAAATCATTTC-CATTG (SEQ ID NO:5) that amplify the ORF29 open reading frame, cutting the PCR product with NheI and NotI, and inserting the fragment into the corresponding sites of pCI (Promega, Madison, Wis.). Plasmid pAc-CMV contains the human cytomegalovirus (CMV) immediate early (IE) promoter inserted into the XhoI-EcoRI site of pAcSG2 (PharMingen). Plasmids pAc-CMV29StuI and pAc-CMV29EeoRV were constructed to produce baculoviruses expressing ORF29. Plasmid pCI-29 was cut with NheI, blunted with the Klenow fragment of *E. coli* DNA polymerase, cut with BamHI and the fragment containing ORF29 and the simian virus 40 (SV40) polyadenylation sequence was inserted into the StuI-BglII site of pAc-CMV to create plasmid pAc-CMV29StuI. This plasmid is predicted to express ORF29 from both the baculo virus polyhedron promoter and the human immediate-early (IE) CMV promoter. Plasmid pCI-29 was cut with BglII, blunted with Klenow, cut with BamHI, and the fragment containing ORF29 driven by the human CMV TE promoter and followed by the SV40 polyadenylation sequence was inserted into the EcoRV-BglII site of pAc-CMV to create plasmid pAc-CMV29EcoRV. This plasmid is predicted to express ORF29 from only the human TE CMV promoter.

VZV cosmids NotI A, NotI B, MstII A, and MstII B encompass the VZV genome (FIG. 1). VZV ORF29, encoded by nucleotides 50,857 to 54,468 of the VZV genome, is predicted to express a protein of 1,204 amino acids (Davison, A. J. et al., 1986, J. Gen. Virol. 67:1759-1816). To construct a virus deleted for ORF29, VZV cosmid MstII B was partially digested with HpaII using the recA-assisted restriction endonuclease cleavage procedure (Ferrin et al., 1991, Science 254:1494-1497). Two single stranded oligonucleotides, CGGGGCCCCTGGGTTACGTT-TATGCGTGCCGGGTTGAAGATTTGGATCTGGA GGAAATTT (SEQ ID NO:6) and GGCGCTTCTT-GAAAAAACGGAAAACTTACCGGAATTATGGAC-TACGGCTTTT ACTTCAAC (SEQ ID NO:7), centered around HpaII sites at nucleotides 50,919 and 53,725 in the VZV genome were annealed to cosmid MstII B using the K *coli* recA protein. Additional HpaII sites in the cosmid were methylated using HpaII methylase and S-adenosylmethinone, and the reaction was heated to 65° C. to remove the oligonucleotide-recA complexes. The DNA was precipitated, cut with HpaII and the large fragment, which lacks most of the ORF29 gene was ligated to itself and was inserted into *E. coli* to produce cosmid VZV MstII B-29D (FIG. 1).

ORF29 was inserted into cosmid MstII A to construct a virus expressing ORF29 at a normative site. VZV cosmid MstII A was digested with AvrII, which cuts at nucleotide 112,853 (between VZV ORFs 65 and 66), and the ends of the cosmid were blunted with Klenow. The BglII-BamHI fragment containing ORF29 from pCI-29 was blunted with Klenow and inserted into the AvrII site of cosmid MstII A. The resulting cosmid MstII A-29 contains the ORF29 gene driven by the human CMV promoter and followed by an SV40 polyadenylation signal (FIG. 1).

Transfections, Southern blotting, immunoblotting, and virus growth studies. VZV cosmids were linearized with NotI or Bsu36I and transfected along with plasmid pCMV62 into human melanoma cells using the calcium phosphate procedure. Cells were passaged each week by treatment with trypsin, and cytopathic effects were noted.

Virion DNA was isolated from nucleocapsids, digested with restriction enzymes, fractionated on 1% agarose gels, transferred to nylon membranes, and probed with a radiolabeled fragment containing ORF29.

Lysates of baculovirus or VZV-infected cells were fractionated on SDS-PAGE gels, transferred to nylon membranes and incubated with rabbit antibody to VZV ORF29 protein, thymidine kinase (a gift from Christine Talarico), IE4, IE63, or IE62, or mouse monoclonal antibody to glycoprotein E (gE) (Chemicon, Temucla, Calif.). (Kinchington, 1988, 1992 cited supra; Moriuchi, H. et al., 1995, Virology 208:376-382; Ng et al., 1994, J. Virol. 68:1350-1359). The blots were incubated with horseradish peroxidase-conjugated anti-rabbit or anti-mouse antibodies and developed with enhanced chemiluminescence (Pierce Chemical Company, Rockford, 111.).

Flasks of melanoma cells were infected with 200 PFU of VZV recombinants and on days 1 to 5 after infection, the cells were treated with trypsin and serial dilutions were titered on melanoma cells. VZV deleted for ORF29 was titered on melanoma cells that had been infected with Baculo 29 the day before. One week after infection, the cells were fixed and stained with crystal violet and plaques were counted.

Four- to 6-week-old female cotton rats were inoculated intramuscularly along the sides of the spine with virus-infected melanoma cells containing $1.75 \times 10^5$ PFU of recombinant VZV. For analysis of acute infection, animals were sacrificed 3 days after infection; for latent infection, animals were sacrificed 5 to 6 weeks after infection. Dorsal root ganglia from the left thoracic and lumbar spine were pooled, DNA was isolated, and PCR was performed using 500 ng of ganglia DNA from infected animals, or serial dilutions of cosmid NotI A in 500 ng of ganglia DNA from uninfected animals (to generate a standard curve), and primers corresponding to ORF21 (Brunell et al., 1999. J. Med. Virol. 58:286-290). The PCR products were fractionated by electrophoresis on agarose gels, transferred to nylon membranes, probed with a radio labeled ORF21 probe, and copy numbers were determined using a phosphorimager. The lower limit of reliable detection was 10 copies per 500 ng of ganglia DNA. PCR was also performed using 500 ng of ganglia DNA and ORF29 primers CATTTTGACCCTGC-CAACAAC (SEQ ID NO:8) and TAGTGCGTGCTCCAGAAACC (SEQ ID NO:9)(the latter sequence is located within the region absent from the ORF29 deletion mutant). Southern blotting was performed, and the membrane was hybridized to a radio labeled ORF29 probe.

RNA from dorsal root ganglia was isolated using Trizol (Invitrogen, Carlsbad, Calif.), treated with DNase I, heated to inactivate DNAse, and cDNA was prepared using oligo (dT) 12-18 and reverse transcriptase. PCR was performed using ORF63 primers (35), and Southern blotting of the amplified DNA was performed using a radiolabeled ORF63 probe.

Results

VZV ORF29 is required for virus replication. Cosmid MstII B-29D was constructed which is deleted for codons 22 to 957 of ORF29. Transfection of melanoma cells with VZV cosmids NotI A, NotI B, MstII A. and MstII B yielded infectious virus (termed VZV ROka) 7 days after infection. However, transfection of cells with cosmids NotI A, NotI B, MstII A, and MstII B-29D failed to yield VZV.

Figure 2:
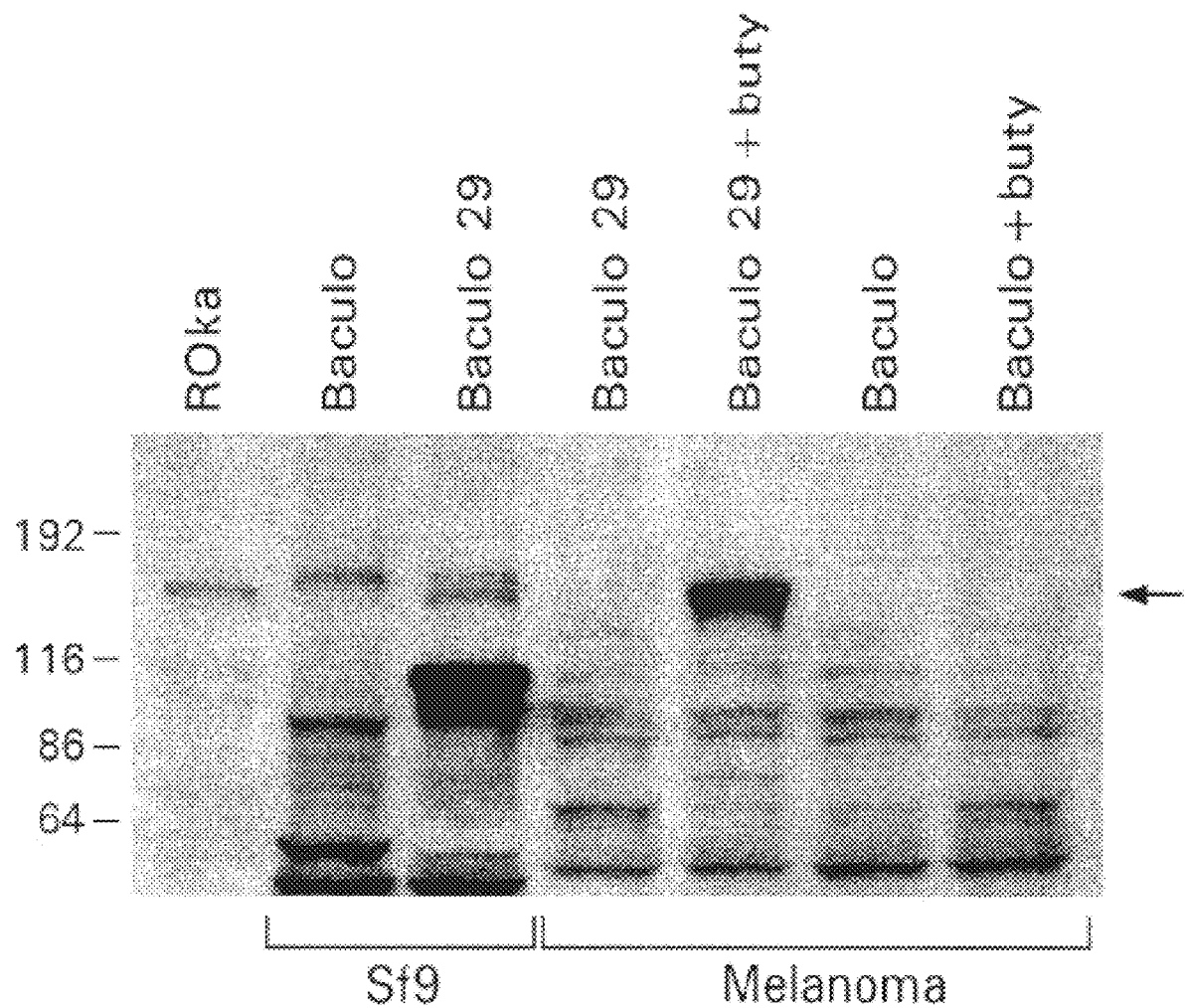
FIG. 2. Expression of ORF29 by recombinant baculo virus. Sf9 cells were infected with control baculo virus (Baculo, lane 2) or baculovirus expressing ORF29 (Baculo 29, lane 3). Melanoma cells were infected with VZV ROka (lane 1), Baculo29 in the absence (lane 4) or presence (lane 5) of sodium butyrate (buty), or control baculovirus in the absence (lane 6) or presence (lane 7) of sodium butyrate.

To complement a VZV ORF29 deletion mutant, we produced baculovirus expressing ORF29. Infection of Sf9 insect cells with Baculo 29 followed by immunoblotting with antibody to ORF29 protein yielded a 130 kDa band (FIG. 2, lane 3). A similar size band was not detected in cells infected with control baculovirus AcNPV. Infection of melanoma cells with Baculo 29 or control baculovirus failed to show a band corresponding to ORF29 protein; however, infection of the cells with VZV ROka showed a band of 130 kDa (FIG. 2, lane 1).

Sodium butyrate is a histone deacetylase inhibitor that enhances expression of foreign genes in mammalian cells when expressed by baculovirus (Condreay J. P. et al., 1999, Proc Natl Acad Sci USA. 96:127-32). Therefore, we treated baculo virus-infected melanoma cells with 5 mM sodium butyrate 1 day before preparing lysates of infected cells. Immunoblotting of Baculo 29-infected cells treated with sodium butyrate showed a band of 130 kDa (FIG. 2, lane 5); no band was detected in cells infected with control baculovirus that had been treated with the chemical.

To construct VZV deleted for ORF29, we infected melanoma cells with Baculo 29 or Baculo 29EcoRV and one hour later transfected the cells with cosmids NotI A, NotI B, MstII A, and MstII B-29D. One week after transfection, the cells were treated with trypsin and additional baculovirus was added to the cells. CPE was detected in melanoma cells 10 days after cosmid transfection of Baculo 29-infected cells and 12 days after transfection of Baculo 29EcoRV-infected cells. Virus obtained from Baculo 29-infected cells was used for all subsequent experiments and was termed VZV ROka29D.

To verify that the deletion in ORF29 did not significantly affect expression of the genes adjacent to ORF29, we constructed cosmid MstII A-29 which contains the ORF29 gene driven by the human CMV promoter. Transfection of cells with cosmids NotI A, NotI B, MstII A-29, and MstII B-29D yielded infectious virus 7 days after transfection. This virus was termed ROka29DR.

Figure 3:
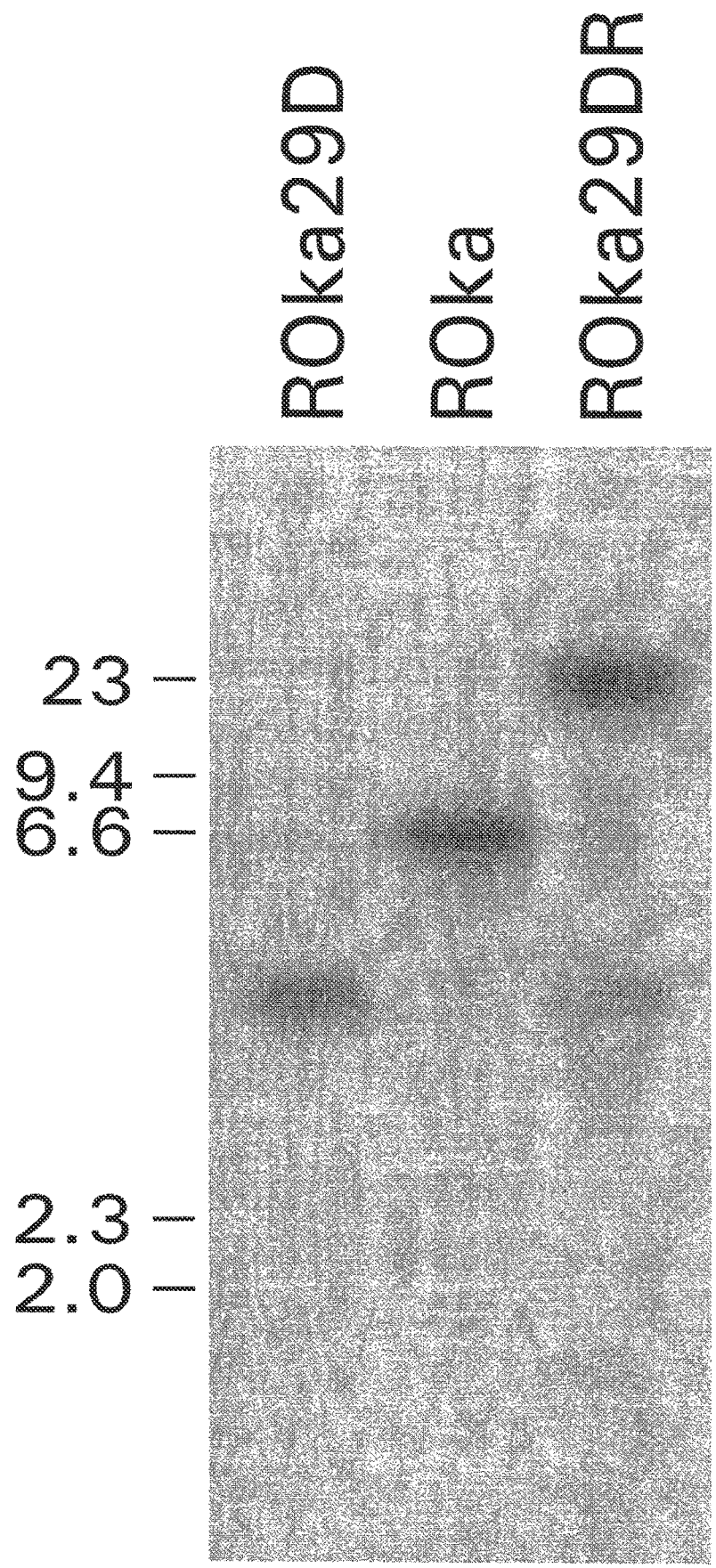
FIG. 3. Southern blot of virion DNA from cells infected with ORF29 mutants. Virion DNA from cells infected with VZV ROka, ROka29D, or ROka29DR was digested with EcoRI and PacI and hybridized with a radiolabeled ORF29 DNA probe. Numbers indicate the sizes of DNAs in kb pairs.

To verify that VZV ROka29D and ROka29DR had the expected genomic structures, Southern blotting was performed. Virion DNA was digested with EcoRI and Pac and hybridized with a radio labeled probe to ORF29. Virion DNA from cells infected with VZV ROka showed a band of 6.5 kb, while cells infected with ROka29D had a band of 3.7 kb due to the 2.8 kb deletion in ORF29 (FIG. 3). Virion DNA from cells infected with VZV ROka29DR had the 2.8 kb band due to the deletion in ORF29 and a new band of 22 due to the insertion of ORF29 into the genome between ORFs 65 and 66.

Figure 4:
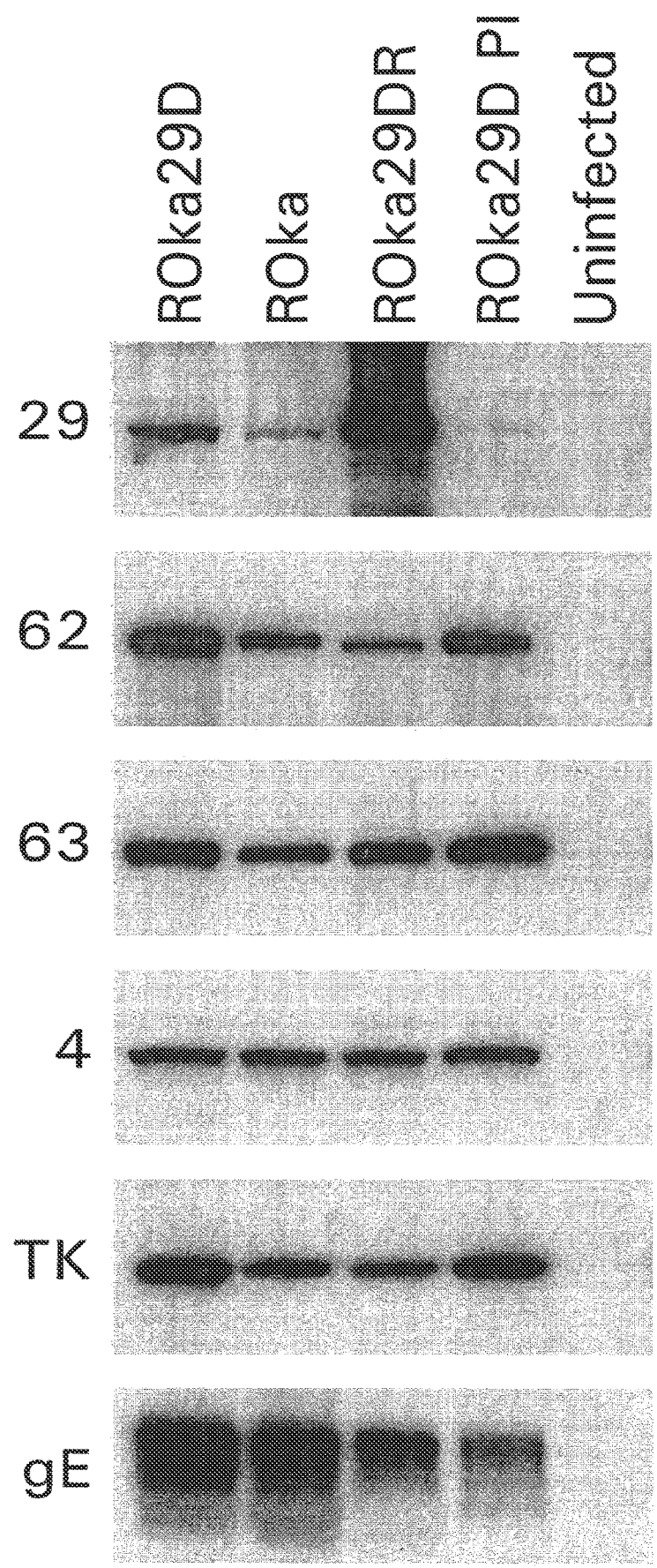
FIG. 4. Immunoblot of lysates from cells infected with ORF29 mutants blotted with antibody to ORF29 protein, IE62, IE63, IE4, VZV thymidine kinase (TK), or gE. Lysates were obtained from cells infected with ROka29D in the presence of Baculo 29 (ROka29D), ROka, ROka29DR, ROka29D after one passage in cells without Baculo 29 (ROka29D P1), or were not infected with any virus. Equivalent amounts of lysates were loaded in each lane and in each panel. Numbers correspond to sizes of proteins in kilodaltons.

Reduced or excessive expression of ORF29 reduces late, but not immediate-early or putative early gene expression. Lysates were prepared from cells infected with ROka, ROka29DR, ROka29D and Baculo 29, or from ROka29D that had been passaged once in cells without Baculo 29, and immunoblotting was performed with several VZV antibodies (FIG. 4). Cells infected with ROka29DR expressed higher levels of ORF29 protein than cells infected with ROka, while cells infected with ROka29D passaged once in cells without Baculo 29 expressed less ORF29 protein than those infected with ROka or ROka29D and Baculo 29.

Expression of VZV IE62, IE63, IE4 and viral thymidine kinase, a putative early gene, were similar in cells infected with ROka, ROka29DR, or ROka29D either in the presence or absence of added Baculo 29. In contrast, expression of VZV gE was reduced in cells infected with ROka29DR or ROka29D passaged once in cells in the absence of Baculo 29, compared with cells infected with ROka. These experiments indicate that appropriate levels of ORF29 protein are required for optimal expression of gE, but not for VZV IE or putative early proteins.

Figure 5:
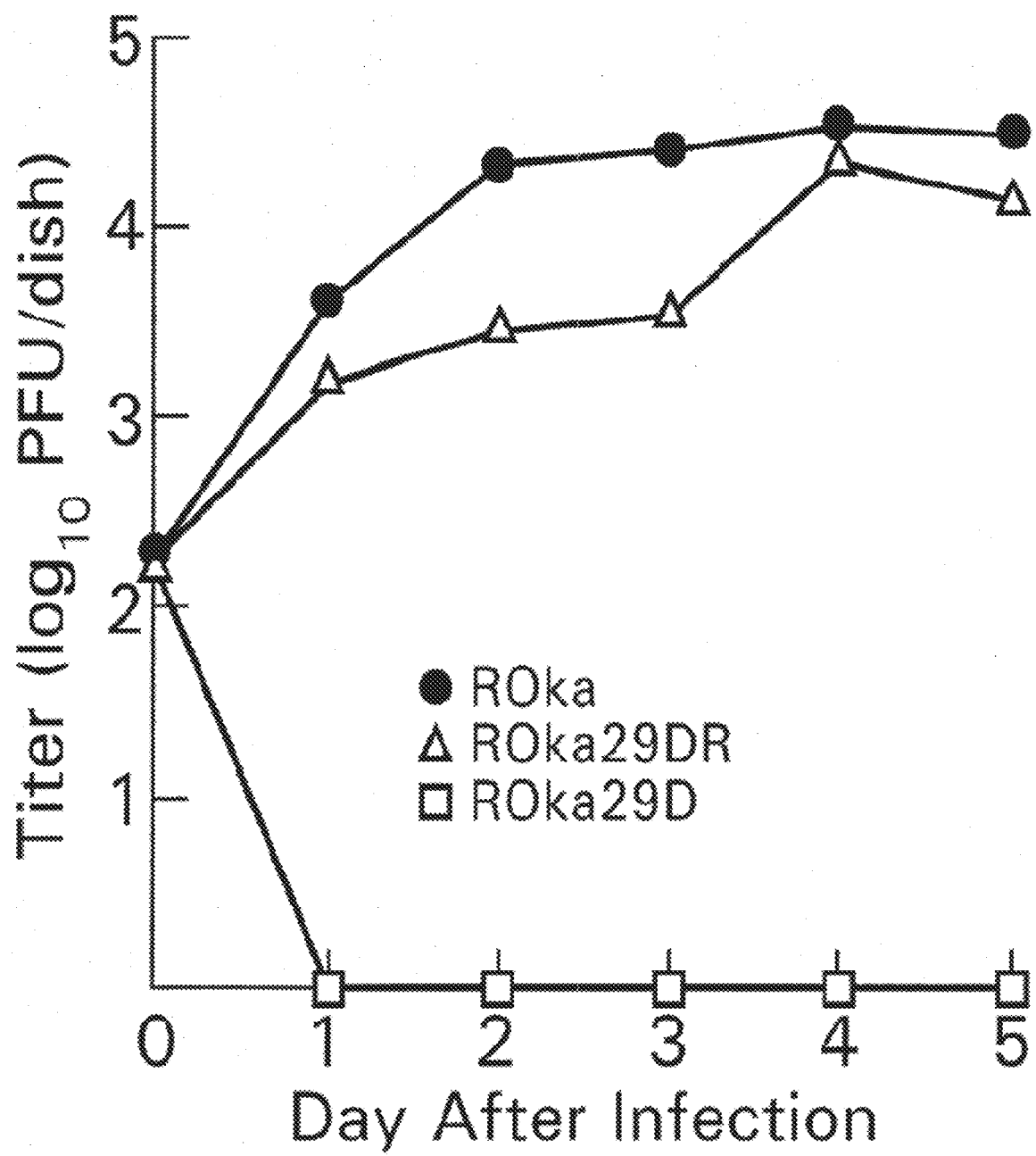
FIG. 5. Growth of ORF29 mutants in melanoma cells. VZV ROka, ROka29D, and ROka29DR were grown in melanoma cells, and at various times the cells were treated with trypsin and virus titers were determined.
Figure 6A:
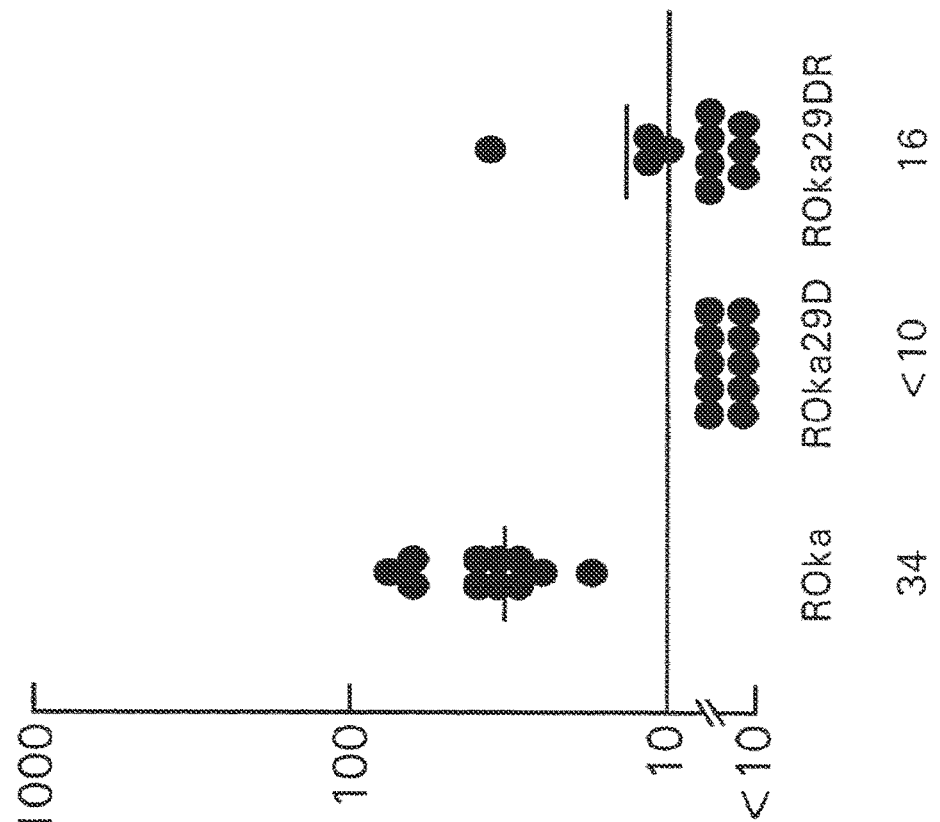
FIGS. 6A-6B. Copy number of VZV genomes in animals latently infected with VZV ROka, ROka29D, or ROka29DR in experiments 1 (FIG. 6A) and 2 (FIG. 6B). The lower limit of detection of viral DNA is 10 copies, and the geometric mean copy number per 500 ng of DNA for the PCR positive ganglia is shown at the bottom.
Figure 6B:
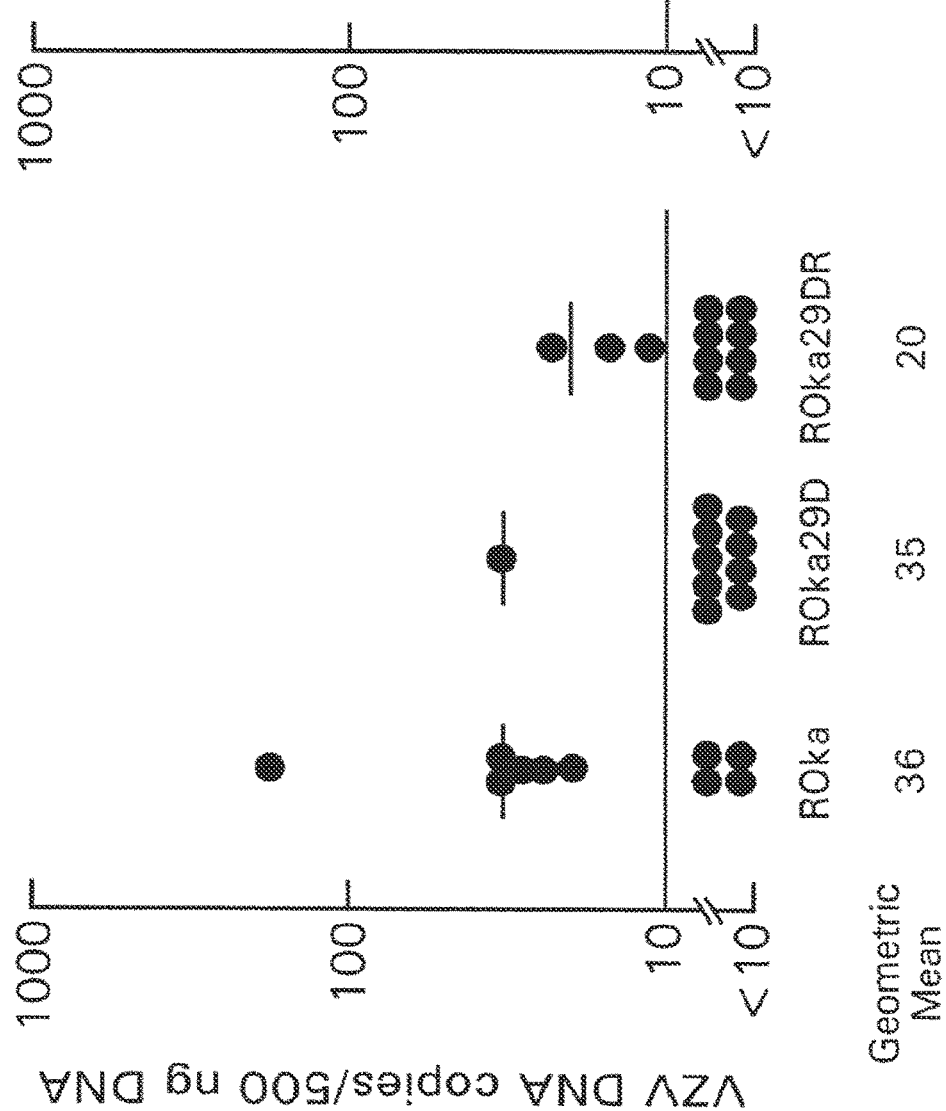
Figure 7:
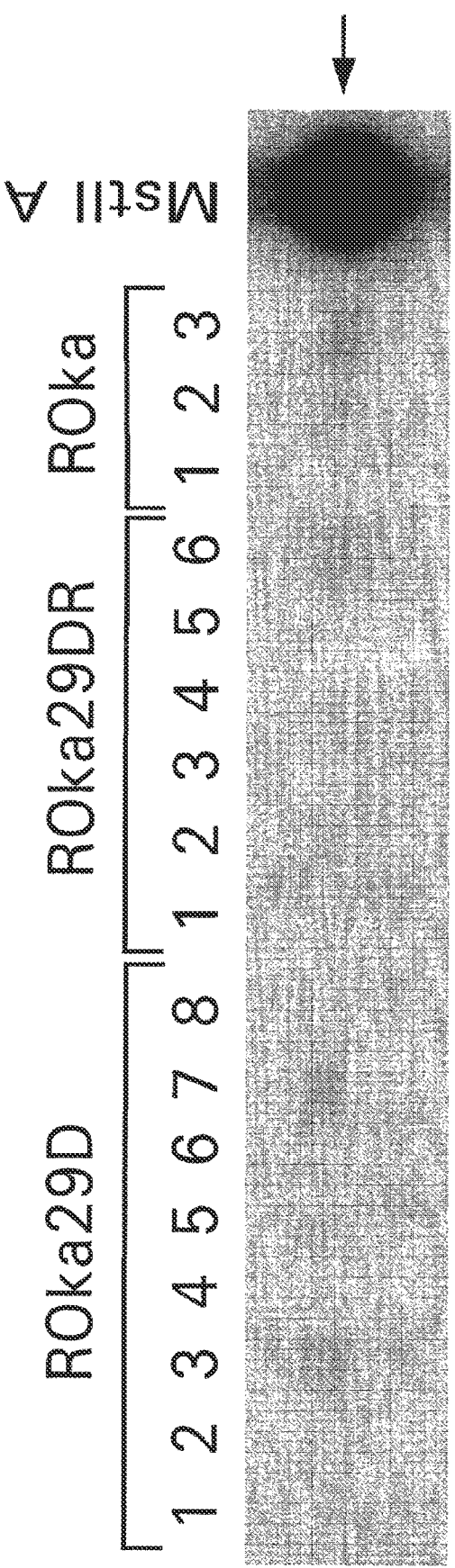
FIG. 7. Southern blot of cDNA corresponding to ORF63 RNA from animals latently infected with ROka29D, ROka29DR, or ROka. RNA was isolated from dorsal root ganglia of infected animals, cDNA was prepared, PCR was performed with primers to ORF63, and the blot was hybridized with a radiolabeled ORF63 probe. Cosmid MstII A, which encodes ORF63, is a positive control.
Figure 8:
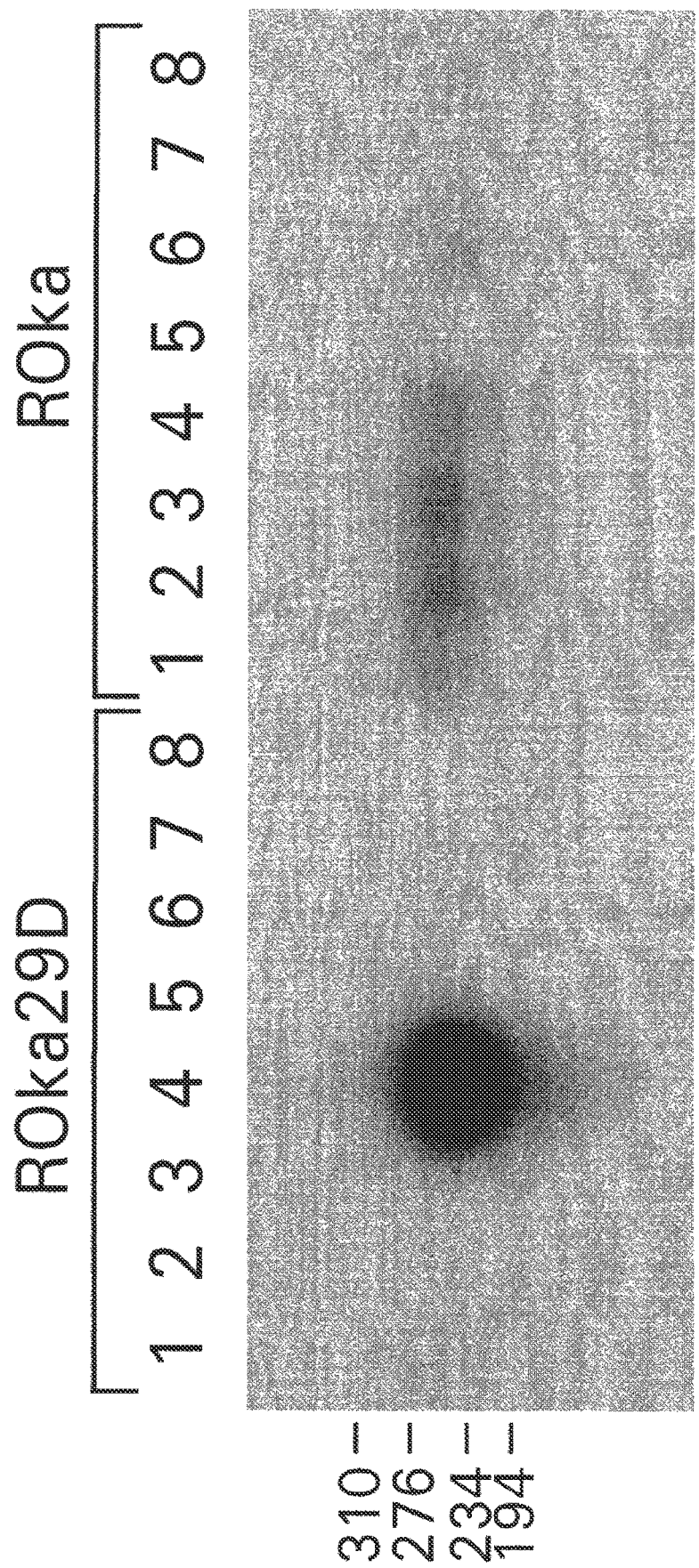
FIG. 8. Southern blot for ORF29 in ganglia of animals latently infected with ROka29D or ROka. Numbers correspond to size of DNA in kilo base pairs.

Growth of VZV ORF29 deletion and repaired virus in cell culture. To study the growth of the ORF29 mutants in cell culture, melanoma cells were infected with the viruses and titers were measured for five consecutive days. VZV deleted for ORF29 was unable to grow in melanoma cells (FIG. 5). VZV ROka29DR, in which ORF29 was driven by the human CMV promoter at a nonnative site in the virus genome, grew slower than ROka, but eventually reached a peak titer that was nearly equivalent to that of ROka.

VZV ORF29 cannot complement HSVICP8, and ICP8 cannot substitute for VZV ORF29. VZV ORF29 is the homolog of HSV-IICP8 and both genes encode single stranded DNA binding proteins. To determine if ORF29 protein can complement HSV-1 ICP8, melanoma cells were infected with Baculo 29, and the following day the cells were infected with HSV d301, which is deleted for ICP8. After incubation for 3 days, no plaques were detected (Table 7). In contrast, wild-type HSV-I produced plaques on these cells.

TABLE 7

Single step growth analysis of VZV ROka,ROka29D, and HSV-1 d301 on Vero, V827, MeWo and MeWo cells infected with Baculo 29[a]

| Cells | Virus | Titer PFU/ml |
| --- | --- | --- |
| Vero cells | ROka | $2.7 \pm 0.3 \times 10^3$ |
|  | ROka29D | <3 |
|  | HSV-1 d301 | <10 |
| V827 cells | ROka | $3.4 + 0.04 \times 10^3$ |
|  | ROka29D | <10 |
|  | HSV d301 | $7.6 \pm 0.5 \times 10^5$ |
| MeWo | HSV d301 | <3 |
| MeWo + Baculo 29 | HSV d301 | <3 |

[a]Vero, V827 cells (Vero cells expressing ICP8 and ICP27), or Me Wo cells were infected at an MOI of 0.03 and incubated at 37° C. for 3 days. VZV-infected cells were treated with trypsin and cell-associated virus was titered, The titer of VZV ROka29D was determined on Me Wo cells infected with Baculo 29 and the titer of ROka was determined on MeWo cells. HSV-infected cells were scraped, freeze-thawed, and media and cell lysates were pooled and titered. The titer of HSV d301 (HSV-1 deleted for ICP8) was determined on V827 cells.

To determine if HSV-1 ICP8 can complement VZV ORF29, Vero cells and Vero cells expressing ICP8 (V827) were infected with VZV deleted for ORF29 and parental virus. While parental virus grew to similar titers on both cell lines, VZV deleted for ORF29 could not grow on either cell line (Table 7). As expected, HSV-1 deleted for ICP8 (HSV-1 d301) grew on V827 cells, but not on Vero cells. The experiment was performed with two different titers of inocula, $0.3 \times 10^4$ PFU (data not shown) and $2.2 \times 10^4$ PFU (data not shown), with similar results.

VZV deleted for ORF29 can infect ganglia. To determine whether VZV ORF29 is required for acute infection of ganglia, cotton rats were infected with ROka29D or ROka and three days later the animals were sacrificed and dorsal root ganglia were obtained and assayed for VZV DNA. All animals infected with VZV ROka29D or ROka had viral DNA in their ganglia. The geometric mean number of VZV genomes in animals acutely infected with ROka29D was 339 copies, and for those infected with ROka the geometric mean number of VZV genomes was 115 copies. (data not shown)

VZV ORF29 is critical for latent infection. To determine if VZV ORF29 is required for establishment of latent infection, cotton rats were inoculated with ROka29D, ROka29DR, or ROka, and 5 to 6 weeks later the animals were sacrificed, DNA was isolated from dorsal root ganglia, and PCR was performed with primers for ORF21 followed by Southern blotting. In the first experiment, 1 of 10 animals infected with VZV ROka29D, 3 of 11 animals infected with ROka 29DR, and 6 of 10 animals infected with ROka had viral DNA in ganglia (FIG. 6A). In the second experiment, none of 10 animals infected with ROka29D, 4 of 11 animals infected with ROka29DR, and 11 of 11 animals infected with ROka had VZV DNA in their ganglia (FIG. 6B). Taken together 5% (1 of 20) of animals infected with ROka29D, 32% (7 of 22) infected with ROka29DR and 81% (17 of 21) infected with ROka were latently infected. When the results of the two experiments were pooled, the difference between animals infected with ROka29D and ROka ($p<0.00001$) and ROka29DR and ROka ($p=0.0044$) were statistically significant, while the difference between animals infected with ROka29D and ROka29DR was barely significant ($p=0.045$).

To verify that animals were latently infected with the ORF29 mutants, RNA was isolated from ganglia on the opposite side of the spinal cord from which DNA had been isolated. cDNA was prepared from the RNA and PCR was performed using primers for ORF63, a gene known to be expressed in VZV latently infected rodent ganglia, followed by Southern blotting. ORF63 RNA was detected in 2 of 8 ganglia from animals infected with ROka29D, 1 of 6 animals with ROka29DR, and 2 of 3 animals infected with ROka (FIG. 7).

The inoculum used to infect animals with ROka29D was prepared by passaging Baculo 29-infected cells that had subsequently been infected with VZV ROka29D, onto uninfected melanoma cells. Therefore, it was possible that recombination might have occurred between Baculo 29 and ROka29D. PCR and Southern blotting for ORF29 using DNA from rodent ganglia showed that 1 of 8 ganglia from animals infected with ROka29D was positive for ORF29, while 5 of 8 animals infected with ROka were positive for ORF29 (FIG. 8). These results imply that recombination between the Baculo 29 and ROka 29D likely occurred in cell culture. Since such a recombinant virus was not detected by Southern blotting (FIG. 3) or by growing the virus on melanoma cells in the absence of Baculo 29 (FIG. 5), this suggests that recombination is a very rare event. These observations are consistent with the fact that 44 flasks (175 $cm^2$ each) were required to prepare the ROka29D inocula for the animal experiments, while each in vitro experiment required 2 or fewer flasks of ROka29D-infected cells.

Discussion

We have shown that ORF29, the major DNA binding protein, is required for replication in cell culture and that the protein cannot complement its HSV-1 homolog. Furthermore, we have found that cells infected with VZV mutants either deleted for ORF29, or that overexpress the protein, are impaired for late gene expression and for establishment of latency in rodents.

ORF29 protein shares a number of features with its HSV-I ICP8 homolog. The two proteins show 65% homology and 49% identity at the amino acid level. Both proteins bind to single stranded DNA and localize to punctate regions within the nucleus (Cohrs, R. J. et al., 2002, J. Virol. 76:7228-38; Kinchington et al, cited supra). ICP8 and ORF29 are essential for replication of HSV and VZV, respectively. (Gao et al., cited supra) However, there are a number of differences between ORF29 protein and ICP8. While ICP8 is a phosphoprotein, ORF29 protein is not phosphorylated. Although HSV ICP8 interacts with UL37 protein, VZV ORF29 protein does not interact with ORF21 protein, its HSV UL37 homolog. VZV ORF29 cannot substitute for ICP8 in an in vitro replication assay using an HSV or VZV origin of replication (Webster, C. B. et al., 1995, Virology 206:655-660). We found that VZV ORF29 protein could not complement the growth of an HSV-1 ICP8 deletion mutant, and that ICP8 could not allow a VZV ORF29 deletion mutant to grow in cell culture. In contrast, HSV-1 ICP8 can complement the growth of an HSV-2 replication defective ICP8 mutant (Da Costa X. J. et al., 1997, Virology 232:1-12). Thus, despite the high degree of homology in their amino acid sequences and their ability to bind to single stranded DNA, VZV ORF29 protein and HSVICP8 are functionally distinct.

Cells infected with VZV deleted for ORF29 expressed similar levels of TE or putative early proteins as cells infected with parental virus, but the level of gE was reduced. Previous studies showed that ORF29 protein has no significant effect on the ability of IE62 to activate the ORF20 or ORF21 promoters and only a modest effect on the ORF28 promoter (Cohrs, 2002, cited supra). While ORF29 protein alone cannot upregulate expression from the gI promoter, ORF29 enhances the ability of ORF62 protein to transactivate the gI promoter (He. H. et al., 2001, Arch. Virol. Suppl. 17:57-60). Our studies show that in the context of the virus, ORF29 protein is important for expression of a late gene, gE. Metabolic labeling studies with an HSV-2 ICP8 replication defective mutant virus showed that proteins of all kinetic classes were expressed at levels similar to or slightly less than parental virus; gB and gD were expressed at lower levels than wild-type virus on immunoblot (Da Costa et al, 1997, cite supra). Surprisingly, we found that overexpression of ORF29 protein during virus infection also resulted in reduced expression of gE. Thus, the level of ORF29 protein must be properly regulated for optimal late gene, but not necessarily immediate-early or early gene expression.

ORF29 is one of six proteins that are expressed during latency in human sensory or cranial nerve ganglia. Previously we showed that ORFs 21 and 66 are not required for establishment of latency, while ORFs 4 and 63 have a critical role in latency (Sato, H., L. et al., 2002, J. Virol. 76:3575-3578; Xia, D. et al., 2003, J. Virol. 77: 1211-1218; Cohen, J. I., et al., 2004, J. Virol. 78:11833-11840; Cohen, J. I. et al., 2005, J. Virol. 79:6969-6975). Here we show that while ORF29 is not required for VZV to enter ganglia, ORF29 is important for efficient establishment of latency in rodents. Similar studies with HSV-2 showed that an ICP8 null mutant was markedly impaired for latency in mice (Jones et al., 2000, Virology 278:137-150).

Overexpression of ORF29 protein, as exemplified by the ROka29DR mutant, was also associated with a significant impairment of VZV latency in rodents. ORF29 protein is present in the nucleus of lytically infected cells, but in the cytoplasm of human neurons during latency (Grinfeld et al, cited supra; Lungu et al., cited supra). Interestingly, when an astrocytoma-derived cell line is infected with adenovirus which expresses ORF29, the protein is expressed in the cytoplasm; however, when these cells are treated with a proteosome inhibitor, the half-life of ORF29 protein is increased and the protein migrates to the nucleus (Stallings et al., 2006, cited supra). Thus, it is possible that overexpression of ORF29 protein in ROka29DR-infected neurons could result in both cytoplasmic and nuclear expression of the protein in the cells and thereby impair latency.

VZV mutants of ORF29 can serve as useful vaccine candidates. Inoculation of mice with the HSV-1 d301 ICP8 deletion mutant virus induces HSV-specific T cell proliferation and protects animals from lethal infection with wild-type virus (Morrison L. A. et al., 1994, J. Virol. 68:689-696; Nguyen, L. H. et al., 1992, J. Virol. 66:7067-7072). Similarly, inoculation of animals with an HSV-21PC8 null mutant reduces acute and latent infection with a challenge virus and protects the animals from death by a challenge virus (Da Costa et al., 2001, cited supra; Jones, C. A. et al., 2000, Virology 278:137-150.). A VZV ORF29 deletion mutant might be useful as a replication defective VZV vaccine, providing that a mutant is made that cannot recombine with the complementing cell line. ROka29DR, which overexpresses the ORF29 protein, and is also impaired for latency, also is a vaccine candidate. This virus is impaired for latency, but has the advantage that none of the viral proteins are deleted and all can be presented to the immune system, albeit at higher or lower levels than with wild-type virus.

It should be noted that, as used in this specification and the appended claims, the singular forms "a", "an" and "the" include plural referents unless the content clearly dictates otherwise. It should also be noted that the term "or" is generally employed in its sense including "and/or" unless the content clearly dictates otherwise.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

The disclosure has been described with reference to various specific and preferred embodiments and techniques. However, it should be understood that many variations and modifications may be made while remaining within the spirit and scope of the disclosure.

REFERENCES

Annunziato, P. W., O. Lungu, C. Panagiotidis, J. H. Zhang, D. N. Silvers, A. A. Gershon, and S. J. Silverstein. 2000. Varicella-zoster virus proteins in skin lesions: implications for a novel role of ORF29p in chickenpox. J. Virol. 74:2005-10.

Boucaud, D., H. Yoshitake, J. Hay, and W. Ruyechan. 1998. The varicella-zoster virus (VZV) open-reading frame 29 protein acts as a modulator of a late VZV gene promoter. J. Infect. Dis. 178 Suppl 1:S34-8.

Brunell, P. A., L. C. Ren, J. 1. Cohen, and S. E. Straus. 1999. Viral gene expression in rat trigeminal ganglia following neonatal infection with varicella-zoster virus. J. Med. Virol. 58:286-290.

Bush, M., D. R. Yager, M. Gao, K. Weisshart, A. I. Marcy, D. M. Coen. and D. M. Knipe. 1991. Correct intranuclear localization of herpes simplex virus DNA polymerase requires the viral ICP8 DNA-binding protein. J. Virol. 65:1082-1089.

Chen, J. J., A. A. Gershon, Z. S. Li, O. Lungu, and M. D. Gershon. 2003. Latent and lytic infection of isolated guinea pig enteric ganglia by varicella zoster virus. J. Med. Virol. 70 Suppl 1:S71-8.

Cohen, J. I., E. Cox, L. Pesnicak, S. Srinivas, and T. Krogmann. 2004. The varicella-zoster virus ORF63 latency-associated protein is critical for establishment of latency. J. Virol. 78:11833-11840.

Cohen, J. I., T. Knogmann, J. P. Ross, L. Pesnicak, and E. Prikhodko, 2005. Varicella-zoster virus ORF4 latency-associated protein is important for establishment of latency. J. Virol. 79:6969-6975.

Cohrs, R. J., M. Barbour, and D. H. Gilden. 1996. Varicella-zoster virus (VZV) transcription during latency in human ganglia: detection of transcripts mapping to genes 21, 29, 62, and 63 in a cDNA library enriched for VZV RNA. J. Virol. 70:2789-%.

Cohrs, R. J., J. Randall, J. Smith, D. H. Gilden, C. Dabrowski. H. van der Keyl, and R. Tal-Singer. 2000. Analysis of individual human trigeminal ganglia for latent herpes simplex virus type 1 and varicella-zoster virus nucleic acids using real-time PCR. J. Virol. 74:11464-11471.

Cohrs, R. J., J. Wischer, C. Essman, and D. H. Gilden. 2002. Characterization of varicella-zoster virus gene 21 and 29 proteins in infected cells. J. Virol. 76:7228-38.

Condreay J. P., S. M. Witherspoon. WC. Clay, and T. A Kost. 1999. Transient and stable gene expression in mammalian cells transduced with a recombinant baculovirus vector. Proc Natl Acad Sci USA. 96:127-32.

Da Costa X. J., N. Boume, L. R. Stanberry, and D. M. Knipe. 1997. Construction and comparison of a replication-defective herpes simplex virus 2 ICP8 mutant strain and its use in immunization studies in a guinea pig model of genital disease. Virology 232:1-12.

Da Costa, X. J., L. A. Morrison, and D. M. Knipe. 2001. Comparison of different forms of herpes simplex replication-defective mutant viruses as vaccines in a mouse model of HSV-2 genital infection. Virology 288:256-63.

Davison, A. J. and J. Scott. 1986. The complete DNA sequence of varicella-zoster virus. J. Gen. Virol. 67:1759-1816.

Ferrin, L. J., and R. D. Camerini-Otero. 1991. Selective cleavage of human DNA: RecA-assisted restriction endonuclease (RARE) cleavage. Science 254:1494-1497.

Gao, M. and D. M. Knipe. 1989. Genetic evidence for multiple nuclear functions of the herpes simplex virus ICP8 DNA-binding protein. J. Virol. 63:5258-5267.

Grinfeld, E. and P. Kennedy. 2004. Translation of varicella-zoster virus genes during human ganglionic latency. Virus Genes 29:317-9.

He, H., D. Boucard, J. Hay, and W. T. Ruyechan. 2001. Cis and trans elements regulating expression of the varicella-zoster virus gI gene. Arch. Virol. Suppl. 17:57-60.

Jones, C. A., T. J. Taylor, and D. M. Knipe. 2000. Biological properties of herpes simplex virus 2 replication defective mutant strains in a murine nasal infection model. Virology 278:137-150.

Kennedy, P. G E., E. Grinfeld, and J. E. Bell. 2000. Varicella-zoster virus gene expression in latently infected and explanted human ganglia. J. Virol. 74:11893-11898.

Kennedy, P. G E., E. Grinfeld, and J. W. Gow. 1999. Latent varicella-zoster virus in human dorsal root ganglia. Virology 258:451-454.

Kennedy, P. G E., E. Grinfeld, S. Bontems, and C. Sadzot-Delvaux. 2001. Varicella-zoster virus gene expression in latently infected rat dorsal root ganglia. Virology 289:218-223.

Kinchington, P. R., J. K. Hougland, A. M. Arvin, W. T. Ruyechan, and J. Hay. 1992. The varicella-zoster virus immediate early protein IE62 is a major component of virus particles. J. Virol. 66:359-366.

Kinchington, P. R., G Inchauspe", J. H. Subak-Sharpe, F. Robey, J. Hay, and W. T. Ruyechan. 1988. Identification and characterization of a varicella-zoster virus DNA-binding protein by using antisera directed against a predicted synthetic oligonucleotide. J. Virol. 62:802-809.

Lungu, O., C. A. Panagintidis, P. W. Annunziato, A. A. Gershon, and S. J. Silverstein. 1998. Aberrant intracellular localization of varicella-zoster virus regulatory proteins during latency. Proc. Natl. Acad. Sci. USA 95:7080-7085.

Meier, J. L., R. P. Holnn, K. D. Croen, J. E. Smialek, and S. E. Straus. 1993. Varicella-zoster virus transcription in human trigeminal ganglia. Virology 193:193-200.

Meier, J. L., X. Luo, M. Sawadogo, and S. E. Straus. 1994. The cellular transcription factor USF cooperates with varicella-zoster virus immediate-early protein 62 to symmetrically activate a bidirectional viral promoter. Mol. Cell Biol. 10:6896-6906.

Meier, J. L. and S. E. Straus. 1993. Varicella-zoster virus DNA polymerase and major DNA-binding protein genes have overlapping divergent promoters. J. Virol. 7:7573-7581.

Moriuchi, H., M. Moriuchi, S. Debrus, J. Piette, and J. I. Cohen. 1995. The acidic amino-terminal region of varicella-zoster open reading frame 4 protein is required for transactivation and can functionally replace the corresponding region of herpes simplex virus ICP27. Virology 208:376-382.

Morrison L. A. and D. M. Knipe. 1994. Immunization with replication-defective mutants of herpes simplex virus type 1: sites of immune intervention in pathogenesis of challenge virus. J. Virol. 68:689-696.

Ng, T. I., L. Keenan, P. R. Kinchington, and C. Grose. 1994. Phosphorylation of varicella-zoster virus open reading frame (ORF) 62 regulatory product by viral ORF47-associated protein kinase. J. Virol. 68:1350-1359.

Nguyen, L. H., D. M. Knipe, and R. W. Finberg. 1992. Replication-defective mutants of herpes simplex virus (HSV) induce cellular immunity and protect against lethal HSV infection. J. Virol. 66:7067-7072.

Ruyechan, W. T. 1983. The major herpes simplex virus DNA-binding protein holds single-stranded DNA in an extended conformation. J. Virol. 46:661-666.

Sadzot-Delvaux, C, S. Debrus, A. Nikkels, J. Piette, and B. Rentier. 1995. Varicella-zoster virus latency in the adult rat is a useful model for human latent infection. Neurology 45 (Suppl 8):S18-S20.

Sato, H., L. Pemicak, and J. I. Cohen. 2002. Varicella-zoster virus open reading frame 2 encodes a membrane phosphoprotein that is dispensable for viral replication and for establishment of latency. J. Virol. 76:3575-3578.

Sato, H., L. Pesicak, and J. I. Cohen. 2003. Varicella-zoster virus ORF47 protein kinase which is required for replication in human T cells, and ORF66 protein kinase which is expressed during latency, are dispensable for establishment of latency. J. Virol. 77:11180-11185.

Stallings, C. L. and S. Silverstein. 2005. Dissection of a novel nuclear localization signal in open reading frame 29 of varicella-zoster virus. J. Virol. 79:13070-10381.

Stallings, C. L., G. J. Duigou, A. A. Gershon, M. D. Gersohn, and S. J. Silverstein. 2006. The cellular localization pattern of varicella-zoster virus ORF29p is influenced by proteosome-mediated degradation. J. Virol. 80:1497-1512.

Webster, C. B., D. Chen, M. Horgan, and P. D. Olivo. 1995. The varicella-zoster virus origin-binding protein can substitute for the herpes simplex virus origin-binding protein in a transient origin-dependent DNA replication assay in insect cells. Virology 206:655-660.

Yang, M., J. Hay, and W. T. Ruyehan. 2004. The DNA element controlling expression of the varicella-zoster virus open reading frame 28 and 29 genes consists of two divergent unidirectional promoters which have a common USF site. J. Virol. 78:10939-52.

Xia, D., S. Srinivas, H. Sato, L. Pesnicak, S. E. Straus, and J. I. Cohen. 2003. Varicella-zoster virus ORF21, which is expressed during latency, is essential for virus replication but dispensable for establishment of latency. J. Virol. 77: 1211-1218.

Zhou, G, V. Galvan, G. Canpdelli-Fiume, and B. Roizman. 2000. Glycoprotein D or J delivered in trans blocks apoptosis in SK-N-SH cells induced by a herpes virus 1 mutant lacking intact genes expressing both glycoproteins. J. Virol. 74:11782-11791.

Each of the above references as well as PCT/US05/021788 is incorporated by reference.

The invention claimed is:

1. A method for making an attenuated live virus having an impaired ability to establish latency, comprising:
   introducing a recombinant virus comprising all or a portion of a herpes virus genome into a host cell to produce an amount of the recombinant virus suitable for a vaccine, wherein the recombinant virus genome comprises a promoter for a latency gene or transcript that is altered or modified, and the gene or transcript is expressed from the recombinant virus genome during viral replication; and
   recovering the recombinant virus from the host cell.

2. The method of claim 1, wherein the herpes virus is selected from the group consisting of herpes simplex virus, varicella-zoster virus (VZV), Marek's disease virus, pseudorabies virus and cytomegalovirus.

3. The method of claim 1, wherein the promoter for the latency gene or transcript is replaced by a heterologous promoter.

4. The method of claim 1, wherein the recombinant virus genome comprises a deletion in a latency gene or transcript at its native location, and the latency gene or transcript is located at a different location in the viral genome and is expressed from a heterologous promoter.

5. The method of claim 1, wherein the latency gene is a VZV gene selected from the group consisting of ORF4, ORF21, ORF29, ORF62, ORF63 and ORF66.

6. The method of claim 5, wherein the latency gene is the VZV ORF29 gene and encodes a major DNA binding protein.

7. The method of claim 1, wherein the recombinant virus lacks all or a portion of a DNA binding protein encoding gene at its native location, the gene being encoded by a nucleic acid sequence that hybridizes to a nucleic acid sequence that encodes a ORF29 protein of VZV.

8. The method of claim 7, wherein the nucleic acid encoding the major DNA binding protein has a deletion of a nucleic acid that encodes at least 10 amino acids.

9. The method of claim 8, wherein amino acids corresponding to amino acids 22-957 of an ORF29 having the amino acid sequence of SEQ ID NO: 3 are deleted.

10. A method for making an attenuated live virus having an impaired ability to establish latency, comprising:
    introducing a recombinant virus comprising all or a portion of a herpes virus genome into a host cell to produce an amount of the recombinant virus suitable for a vaccine, wherein the recombinant virus genome comprises a latency gene or transcript and the latency gene or transcript is at a different location in the genome relative to its native location; and
    recovering the recombinant virus from the host cell.

11. The method of claim 10, wherein the latency gene or transcript comprises at least one mutation.

12. The method of claim 11, wherein the latency gene is VZV ORF29 and the mutation is a deletion or substitution in the nuclear localization sequence that impairs the ability of ORF29 to translocate to the nucleus.

13. The method of claim 10, wherein the latency gene is located in a position corresponding to that between ORF65 and ORF66 of VZV.

* * * * *

SEQUENCE LISTING

```
<160> NUMBER OF SEQ ID NOS: 11

<210> SEQ ID NO 1
<211> LENGTH: 3615
<212> TYPE: DNA
<213> ORGANISM: Varicella zoster

<400> SEQUENCE: 1
atggaaaata ctcagaagac tgtgacagtg cccacggggc ccctgggtta cgtttatgcg    60
```

```
tgccgggttg aagatttgga tctggaggaa atttcatttt tggccgctcg tagcacggac    120
tctgatttgg ctttattacc tttgatgcgt aatttgaccg tggaaaaaac ttttacatcc    180
agcctggcgg tggtttctgg agcacgcact acgggtcttg ccggagctgg tattaccta     240 aaactcacta ccagtcattt ctatccatct gtctttgtct ttcacggagg caaacacgtt    300
ttacccagct ccgcggcccc aaatctcaca cgcgcgtgta acgcggctcg agaacggttt    360
gggttttcac gctgccaagg gcctcctgtt gacggtgctg ttgagacgac cggcgctgag    420
atatgcaccc gccttggatt agagccagaa aatacaatat tatacttggt ggtcacggca    480
ttgtttaagg aagccgtatt tatgtgcaac gtgtttctgc attatggagg actcgatatt    540
gttcatatta accatgggga tgttatacgt ataccgttat ttccggtaca acttttcatg    600
cccgatgtta accgtctggt acccgaccca ttcaacactc atcacaggtc tatcggagag    660
ggttttgtat acccaacacc cttttataac accgggttgt gccatttaat acatgactgt    720
gttattgctc ccatggccgt tgccttgcgc gtcagaaatg taactgccgt cgcccgagga    780
gcggcccacc ttgcttttga tgaaaatcac gaggggcag tactccccc tgacattacg      840 tacacgtatt ttcagtcctc ttcaagtgga accactaccg cccgtggagc gcgtcgaaac    900
gatgtcaact ccacgtctaa gcctagccca tcgggggggt ttgaaagacg gttggcgtct    960
attatggccg ctgacacagc cttgcacgca gaagttatat tcaacactgg aatttacgaa    1020
gaaactccaa cagatatcaa agaatggcca atgtttatag gcatggaggg cactttgcca    1080
aggctaaacg ctctggggtc atataccgct cgtgtggccg gggtcattgg tgcgatggtt    1140
ttcagcccaa attctgcgtt gtatctaact gaggtggagg atagcgggat gaccgaagcc    1200
aaggatgggg gaccgggtcc atcatttaat cgattttacc agtttgccgg acctcattta    1260
gctgcgaatc cccaaacaga tcgagatggc cacgttctat ccagtcagtc tacgggttca    1320
tcaaacacag agtttagcgt ggattatttg cactcattt gtggatttgg agcaccctg     1380 ttggcgcgac tgctttttta tctagaacgc tgtgacgctg gtgcgtttac aggggtcac    1440 ggggatgcgt taaaatatgt tacggggacc tttgactctg aaattccatg tagtttatgt    1500
gaaaaacaca cgcggccggt atgcgctcac acaacagtac accgacttag acaacgcatg    1560
ccgcgatttg acaagccac ccgtcaacct attggggtgt ttggaacaat gaacagccaa     1620
tatagcgact gcgatcctct aggaaactat gctccatatt taatccttcg aaaacccggg    1680
gatcaaacgg aagcagcaaa ggcaaccatg caggacactt atagggctac actagaacgc    1740
ttgtttatcg atctagaaca agagcgacta ctggatcgcg gtgccccatg ttcttccgag    1800
ggactatcgt ctgtcattgt ggatcatcca acgtttcgtc gcatattaga cacactgcgt    1860
gcgcgtatag aacagacaac aacacaattt atgaaagtgt tggttgagac ccgcgattat    1920
aagatccgtg aaggattatc cgaagccacc cattcaatgg cgttaacgtt tgatccatac    1980
tcaggagcat tttgtcccat taccaatttt ttagttaaac gaaacacacct agccgtggta    2040 caagacttag cattaagcca atgtcattgt gtattttacg acagcaagt tgaggggcgg     2100 aactttcgta accaattcca acctgttttg cggcggcgtt tgttgacct gtttaatggg    2160 gggtttatat caacacgctc tataaccgta acattatctg aaggtcctgt atccgcccca    2220
aatccgacat tgggacaaga cgcgcccgcg gggcgtacct ttgatgggga tttagcgcgc    2280
gtaagcgtgg aagttattcg ggatatacga gttaaaaata gggtcgtttt ttcaggtaac    2340
tgtacaaatc tctctgaggc agcccgggca aggcttgtag gccttgcaag tgcgtaccaa    2400
```

```
cgccaagaaa aaagagtgga tatgttacac ggggccctag ggttttttgct taaacagttt    2460 cacggcctgt tatttcctcg gggtatgcca ccaaacagta aatcccccaa cccgcagtgg    2520
ttttggaccc tgttacaacg caaccagatg ccggcagata aacttacaca cgaagagatt    2580
accactattg cagctgttaa acggtttacc gaggaatatg cagcaataaa ctttattaat    2640 ctaccccccaa cctgcatagg agaattagcc cagtttttata tggcaaatct tattcttaaa   2700
tactgcgatc attcacagta ccttataaat accttaactt ctataattac gggtgccagg    2760
cgcccgcgtg acccatcatc cgttttgcat tggattcgta aagatgtcac gtccgccgcg    2820
gacatagaaa cccaagcaaa ggcgcttctt gaaaaaacgg aaaacttacc ggaattatgg    2880
actacggctt ttacttcaac tcatttagtc cgcgcggcca tgaatcaacg tcccatggtc    2940
gttttaggaa taagcattag taaatatcac ggagcggcag aaacaaccg cgtcttttcag    3000 gcagggaatt ggagcggttt aaacgggggt aaaaatgtat gcccgctatt tacatttgat    3060
cgcactcgcc gttttataat agcatgtcct agaggaggtt ttatctgccc cgtaacaggt    3120
ccctcgtcgg gaaatcgaga aaccaccta tccgaccaag ttcgcggtat aattgtcagt    3180
ggcggggcca tggttcaatt agccatatac gccacggttg tgcgtgcagt gggcgctcga    3240
gcacaacata tggcatttga cgactggtta agtcttacag cgatgagtt tttagccaga    3300 gacttggagg agttacacga ccagattatc caaaccctgg aaacgccctg accgtagaa    3360 ggcgctctag aagcagtaaa gattctagat gaaaaaacga cagcgggaga tggggaaacc    3420
cccacaaacc tagcatttaa ttttgattct tgtgaaccaa gccatgacac cacatctaac    3480
gtattaaaca tttcagggtc aaacatttca gggtcaactg tccctggtct taaacgaccc    3540
cccgaagatg acgaactctt tgatcttagt ggtattccca taaaacatgg gaacattaca    3600
atggaaatga tttaa                                                     3615

<210> SEQ ID NO 2
<211> LENGTH: 808
<212> TYPE: DNA
<213> ORGANISM: Varicella zoster

<400> SEQUENCE: 2
atggaaaata ctcagaagac tgtgacagtg cccacggggc ccctgggtta cgtttatgcg     60
tgcggaatta tggactacgg cttttacttc aactcattta gtccgcgcgg ccatgaatca    120
acgtcccatg gtcgttttag gaataagcat tagtaaatat cacggagcgg caggaaacaa    180
ccgcgtcttt caggcaggga attggagcgg tttaaacggg ggtaaaaatg tatgcccgct    240
atttacattt gatcgcactc gccgttttat aatagcatgt cctagaggag gttttatctg    300
ccccgtaaca ggtccctcgt cgggaaatcg agaaaccacc ctatccgacc aagttcgcgg    360
tataattgtc agtggcgggg ccatggttca attagccata cgccacgg ttgtgcgtgc    420 agtgggcgct cgagcacaac atatggcatt tgacgactgg ttaagtctta cagacgatga    480 gttttttagcc agagacttgg aggagttaca cgaccagatt atccaaaccc tggaaacgcc    540
ctggaccgta gaaggcgctc tagaagcagt aaagattcta gatgaaaaaa cgacagcggg    600
agatggggaa ccccacaaa cctagcatt taatttttgat tcttgtgaac caagccatga    660
caccacatct aacgtattaa acatttcagg gtcaaacatt tcagggtcaa ctgtccctgg    720
tcttaaacga ccccccgaag atgacgaact cttttgatctt agtggtattc ccataaaaca    780
tgggaacatt acaatggaaa tgatttaa                                       808
```

<210> SEQ ID NO 3
<211> LENGTH: 1204
<212> TYPE: PRT
<213> ORGANISM: Varicella zoster

<400> SEQUENCE: 3

```
Met Glu Asn Thr Gln Lys Thr Val Thr Val Pro Thr Gly Pro Leu Gly
1               5                   10                  15

Tyr Val Tyr Ala Cys Arg Val Glu Asp Leu Asp Leu Glu Glu Ile Ser
            20                  25                  30

Phe Leu Ala Ala Arg Ser Thr Asp Ser Asp Leu Ala Leu Leu Pro Leu
        35                  40                  45

Met Arg Asn Leu Thr Val Glu Lys Thr Phe Thr Ser Ser Leu Ala Val
    50                  55                  60

Val Ser Gly Ala Arg Thr Thr Gly Leu Ala Gly Ala Gly Ile Thr Leu
65                  70                  75                  80

Lys Leu Thr Thr Ser His Phe Tyr Pro Ser Val Phe Val Phe His Gly
                85                  90                  95

Gly Lys His Val Leu Pro Ser Ser Ala Ala Pro Asn Leu Thr Arg Ala
            100                 105                 110

Cys Asn Ala Ala Arg Glu Arg Phe Gly Phe Ser Arg Cys Gln Gly Pro
        115                 120                 125

Pro Val Asp Gly Ala Val Glu Thr Thr Gly Ala Glu Ile Cys Thr Arg
    130                 135                 140

Leu Gly Leu Glu Pro Glu Asn Thr Ile Leu Tyr Leu Val Thr Ala
145                 150                 155             160

Leu Phe Lys Glu Ala Val Phe Met Cys Asn Val Phe Leu His Tyr Gly
                165                 170                 175

Gly Leu Asp Ile Val His Ile Asn His Gly Asp Val Ile Arg Ile Pro
            180                 185                 190

Leu Phe Pro Val Gln Leu Phe Met Pro Asp Val Asn Arg Leu Val Pro
        195                 200                 205

Asp Pro Phe Asn Thr His His Arg Ser Ile Gly Glu Gly Phe Val Tyr
    210                 215                 220

Pro Thr Pro Phe Tyr Asn Thr Gly Leu Cys His Leu Ile His Asp Cys
225                 230                 235                 240

Val Ile Ala Pro Met Ala Val Ala Leu Arg Val Arg Asn Val Thr Ala
                245                 250                 255

Val Ala Arg Gly Ala Ala His Leu Ala Phe Asp Glu Asn His Glu Gly
            260                 265                 270

Ala Val Leu Pro Pro Asp Ile Thr Tyr Thr Tyr Phe Gln Ser Ser Ser
        275                 280                 285

Ser Gly Thr Thr Thr Ala Arg Gly Ala Arg Arg Asn Asp Val Asn Ser
    290                 295                 300

Thr Ser Lys Pro Ser Pro Ser Gly Gly Phe Glu Arg Arg Leu Ala Ser
305                 310                 315                 320

Ile Met Ala Ala Asp Thr Ala Leu His Ala Glu Val Ile Phe Asn Thr
                325                 330                 335

Gly Ile Tyr Glu Glu Thr Pro Thr Asp Ile Lys Glu Trp Pro Met Phe
            340                 345                 350

Ile Gly Met Glu Gly Thr Leu Pro Arg Leu Asn Ala Leu Gly Ser Tyr
        355                 360                 365

Thr Ala Arg Val Ala Gly Val Ile Gly Ala Met Val Phe Ser Pro Asn
    370                 375                 380
```

-continued

```
Ser Ala Leu Tyr Leu Thr Glu Val Glu Asp Ser Gly Met Thr Glu Ala
385                 390                 395                 400

Lys Asp Gly Gly Pro Gly Pro Ser Phe Asn Arg Phe Tyr Gln Phe Ala
                405                 410                 415

Gly Pro His Leu Ala Ala Asn Pro Gln Thr Asp Arg Asp Gly His Val
            420                 425                 430

Leu Ser Ser Gln Ser Thr Gly Ser Ser Asn Thr Glu Phe Ser Val Asp
        435                 440                 445

Tyr Leu Ala Leu Ile Cys Gly Phe Gly Ala Pro Leu Leu Ala Arg Leu
    450                 455                 460

Leu Phe Tyr Leu Glu Arg Cys Asp Ala Gly Ala Phe Thr Gly Gly His
465                 470                 475                 480

Gly Asp Ala Leu Lys Tyr Val Thr Gly Thr Phe Asp Ser Glu Ile Pro
                485                 490                 495

Cys Ser Leu Cys Glu Lys His Thr Arg Pro Val Cys Ala His Thr Thr
                500                 505                 510

Val His Arg Leu Arg Gln Arg Met Pro Arg Phe Gly Ala Thr Arg
        515                 520                 525

Gln Pro Ile Gly Val Phe Gly Thr Met Asn Ser Gln Tyr Ser Asp Cys
    530                 535                 540

Asp Pro Leu Gly Asn Tyr Ala Pro Tyr Leu Ile Leu Arg Lys Pro Gly
545                 550                 555                 560

Asp Gln Thr Glu Ala Ala Lys Ala Thr Met Gln Asp Thr Tyr Arg Ala
                565                 570                 575

Thr Leu Glu Arg Leu Phe Ile Asp Leu Glu Gln Glu Arg Leu Leu Asp
            580                 585                 590

Arg Gly Ala Pro Cys Ser Ser Glu Gly Leu Ser Ser Val Ile Val Asp
        595                 600                 605

His Pro Thr Phe Arg Arg Ile Leu Asp Thr Leu Arg Ala Arg Ile Glu
    610                 615                 620

Gln Thr Thr Thr Gln Phe Met Lys Val Leu Val Glu Thr Arg Asp Tyr
625                 630                 635                 640

Lys Ile Arg Glu Gly Leu Ser Glu Ala Thr His Ser Met Ala Leu Thr
                645                 650                 655

Phe Asp Pro Tyr Ser Gly Ala Phe Cys Pro Ile Thr Asn Phe Leu Val
            660                 665                 670

Lys Arg Thr His Leu Ala Val Val Gln Asp Leu Ala Leu Ser Gln Cys
        675                 680                 685

His Cys Val Phe Tyr Gly Gln Gln Val Glu Gly Arg Asn Phe Arg Asn
    690                 695                 700

Gln Phe Gln Pro Val Leu Arg Arg Phe Val Asp Leu Phe Asn Gly
705                 710                 715                 720

Gly Phe Ile Ser Thr Arg Ser Ile Thr Val Thr Leu Ser Glu Gly Pro
                725                 730                 735

Val Ser Ala Pro Asn Pro Thr Leu Gly Gln Asp Ala Pro Ala Gly Arg
            740                 745                 750

Thr Phe Asp Gly Asp Leu Ala Arg Val Ser Val Glu Val Ile Arg Asp
        755                 760                 765

Ile Arg Val Lys Asn Arg Val Phe Ser Gly Asn Cys Thr Asn Leu
    770                 775                 780

Ser Glu Ala Ala Arg Ala Arg Leu Val Gly Leu Ala Ser Ala Tyr Gln
785                 790                 795                 800

Arg Gln Glu Lys Arg Val Asp Met Leu His Gly Ala Leu Gly Phe Leu
```

Leu Lys Gln Phe His Gly Leu Leu Phe Pro Arg Gly Met Pro Pro Asn
    805                 810                 815

Ser Lys Ser Pro Asn Pro Gln Trp Phe Trp Thr Leu Leu Gln Arg Asn
820                 825                 830

Gln Met Pro Ala Asp Lys Leu Thr His Glu Glu Ile Thr Thr Ile Ala
835                 840                 845

Ala Val Lys Arg Phe Thr Glu Glu Tyr Ala Ala Ile Asn Phe Ile Asn
850                 855                 860

Leu Pro Pro Thr Cys Ile Gly Glu Leu Ala Gln Phe Tyr Met Ala Asn
865                 870                 875                 880

Leu Ile Leu Lys Tyr Cys Asp His Ser Gln Tyr Leu Ile Asn Thr Leu
    885                 890                 895

Thr Ser Ile Ile Thr Gly Ala Arg Arg Pro Arg Asp Pro Ser Ser Val
    900                 905                 910

Leu His Trp Ile Arg Lys Asp Val Thr Ser Ala Ala Asp Ile Glu Thr
    915                 920                 925

Gln Ala Lys Ala Leu Leu Glu Lys Thr Glu Asn Leu Pro Glu Leu Trp
930                 935                 940

Thr Thr Ala Phe Thr Ser Thr His Leu Val Arg Ala Ala Met Asn Gln
945                 950                 955                 960

Arg Pro Met Val Val Leu Gly Ser Ile Ser Lys Tyr His Gly Ala
    965                 970                 975

Ala Gly Asn Asn Arg Val Phe Gln Ala Gly Asn Trp Ser Gly Leu Asn
    980                 985                 990

Gly Gly Lys Asn Val Cys Pro Leu Phe Thr Phe Asp Arg Thr Arg
    995                 1000                1005

Arg Phe Ile Ile Ala Cys Pro Arg Gly Gly Phe Ile Cys Pro Val
    1010                1015                1020

Thr Gly Pro Ser Ser Gly Asn Arg Glu Thr Thr Leu Ser Asp Gln
    1025                1030                1035

Val Arg Gly Ile Ile Val Ser Gly Gly Ala Met Val Gln Leu Ala
    1040                1045                1050

Ile Tyr Ala Thr Val Val Arg Ala Val Gly Ala Arg Ala Gln His
    1055                1060                1065

Met Ala Phe Asp Asp Trp Leu Ser Leu Thr Asp Asp Glu Phe Leu
    1070                1075                1080

Ala Arg Asp Leu Glu Glu Leu His Asp Gln Ile Ile Gln Thr Leu
    1085                1090                1095

Glu Thr Pro Trp Thr Val Glu Gly Ala Leu Glu Ala Val Lys Ile
    1100                1105                1110

Leu Asp Glu Lys Thr Thr Ala Gly Asp Gly Glu Thr Pro Thr Asn
    1115                1120                1125

Leu Ala Phe Asn Phe Asp Ser Cys Glu Pro Ser His Asp Thr Thr
    1130                1135                1140

Ser Asn Val Leu Asn Ile Ser Gly Ser Asn Ile Ser Gly Ser Thr
    1145                1150                1155

Val Pro Gly Leu Lys Arg Pro Pro Glu Asp Asp Glu Leu Phe Asp
    1160                1165                1170

Leu Ser Gly Ile Pro Ile Lys His Gly Asn Ile Thr Met Glu Met
    1175                1180                1185
                1190                1195                1200

Ile

```
<210> SEQ ID NO 4
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 4
gcctagctag ccaaaatgga aaatactcag aagactgtg                    39

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
gtcagaatgc ggccgcggga ggttaaatca tttccattg                    39

<210> SEQ ID NO 6
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 6
cggggcccct gggttacgtt tatgcgtgcc gggttgaaga tttggatctg gaggaaattt    60

<210> SEQ ID NO 7
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 7
ggcgcttctt gaaaaaacgg aaaacttacc ggaattatgg actacggctt ttacttcaac    60

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
catttgaccc tgccaacaac                                         20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tagtgcgtgc tccagaaacc                                         20

<210> SEQ ID NO 10
<211> LENGTH: 1204
<212> TYPE: PRT
<213> ORGANISM: Varicella zoster

<400> SEQUENCE: 10
```

```
Met Glu Asn Thr Gln Lys Thr Val Thr Val Pro Thr Gly Pro Leu Gly
1               5                   10                  15

Tyr Val Tyr Ala Cys Arg Val Glu Asp Leu Asp Leu Glu Ile Ser
            20                  25                  30

Phe Leu Ala Ala Arg Ser Thr Asp Ser Asp Leu Ala Leu Leu Pro Leu
        35                  40                  45

Met Arg Asn Leu Thr Val Glu Lys Thr Phe Thr Ser Ser Leu Ala Val
    50                  55                  60

Val Ser Gly Ala Arg Thr Thr Gly Leu Ala Gly Ala Gly Ile Thr Leu
65                  70                  75                  80

Lys Leu Thr Thr Ser His Phe Tyr Pro Ser Val Phe Val Phe His Gly
                85                  90                  95

Gly Lys His Val Leu Pro Ser Ser Ala Ala Pro Asn Leu Thr Arg Ala
            100                 105                 110

Cys Asn Ala Ala Arg Glu Arg Phe Gly Phe Ser Arg Cys Gln Gly Pro
        115                 120                 125

Pro Val Asp Gly Ala Val Glu Thr Thr Gly Ala Glu Ile Cys Thr Arg
    130                 135                 140

Leu Gly Leu Glu Pro Glu Asn Thr Ile Leu Tyr Leu Val Val Thr Ala
145                 150                 155                 160

Leu Phe Lys Glu Ala Val Phe Met Cys Asn Val Phe Leu His Tyr Gly
                165                 170                 175

Gly Leu Asp Ile Val His Ile Asn His Gly Asp Val Ile Arg Ile Pro
            180                 185                 190

Leu Phe Pro Val Gln Leu Phe Met Pro Asp Val Asn Arg Leu Val Pro
        195                 200                 205

Asp Pro Phe Asn Thr His Arg Ser Ile Gly Glu Gly Phe Val Tyr
    210                 215                 220

Pro Thr Pro Phe Tyr Asn Thr Gly Leu Cys His Leu Ile His Asp Cys
225                 230                 235                 240

Val Ile Ala Pro Met Ala Val Ala Leu Arg Val Arg Asn Val Thr Ala
                245                 250                 255

Val Ala Arg Gly Ala Ala His Leu Ala Phe Asp Glu Asn His Glu Gly
            260                 265                 270

Ala Val Leu Pro Pro Asp Ile Thr Tyr Thr Tyr Phe Gln Ser Ser Ser
        275                 280                 285

Ser Gly Thr Thr Thr Ala Arg Gly Ala Arg Arg Asn Asp Val Asn Ser
    290                 295                 300

Thr Ser Lys Pro Ser Pro Ser Gly Gly Phe Glu Arg Arg Leu Ala Ser
305                 310                 315                 320

Ile Met Ala Ala Asp Thr Ala Leu His Ala Glu Val Ile Phe Asn Thr
                325                 330                 335

Gly Ile Tyr Glu Glu Thr Pro Thr Asp Ile Lys Glu Trp Pro Met Phe
            340                 345                 350

Ile Gly Met Glu Gly Thr Leu Pro Arg Leu Asn Ala Leu Gly Ser Tyr
        355                 360                 365

Thr Ala Arg Val Ala Gly Val Ile Gly Ala Met Val Phe Ser Pro Asn
    370                 375                 380

Ser Ala Leu Tyr Leu Thr Glu Val Glu Asp Ser Gly Met Thr Glu Ala
385                 390                 395                 400

Lys Asp Gly Gly Pro Gly Pro Ser Phe Asn Arg Phe Tyr Gln Phe Ala
                405                 410                 415
```

-continued

```
Gly Pro His Leu Ala Ala Asn Pro Gln Thr Asp Arg Asp Gly His Val
            420                 425                 430

Leu Ser Ser Gln Ser Thr Gly Ser Ser Asn Thr Glu Phe Ser Val Asp
            435                 440                 445

Tyr Leu Ala Leu Ile Cys Gly Phe Gly Ala Pro Leu Leu Ala Arg Leu
            450                 455                 460

Leu Phe Tyr Leu Glu Arg Cys Asp Ala Gly Ala Phe Thr Gly Gly His
465                 470                 475                 480

Gly Asp Ala Leu Lys Tyr Val Thr Gly Thr Phe Asp Ser Glu Ile Pro
                485                 490                 495

Cys Ser Leu Cys Glu Lys His Thr Arg Pro Val Cys Ala His Thr Thr
                500                 505                 510

Val His Arg Leu Arg Gln Arg Met Pro Arg Phe Gly Gln Ala Thr Arg
            515                 520                 525

Gln Pro Ile Gly Val Phe Gly Thr Met Asn Ser Gln Tyr Ser Asp Cys
            530                 535                 540

Asp Pro Leu Gly Asn Tyr Ala Pro Tyr Leu Ile Leu Arg Lys Pro Gly
545                 550                 555                 560

Asp Gln Thr Glu Ala Ala Lys Ala Thr Met Gln Asp Thr Tyr Arg Ala
                565                 570                 575

Thr Leu Glu Arg Leu Phe Ile Asp Leu Glu Gln Glu Arg Leu Leu Asp
            580                 585                 590

Arg Gly Ala Pro Cys Ser Ser Glu Gly Leu Ser Ser Val Ile Val Asp
            595                 600                 605

His Pro Thr Phe Arg Arg Ile Leu Asp Thr Leu Arg Ala Arg Ile Glu
610                 615                 620

Gln Thr Thr Thr Gln Phe Met Lys Val Leu Val Glu Thr Arg Asp Tyr
625                 630                 635                 640

Lys Ile Arg Glu Gly Leu Ser Glu Ala Thr His Ser Met Ala Leu Thr
                645                 650                 655

Phe Asp Pro Tyr Ser Gly Ala Phe Cys Pro Ile Thr Asn Phe Leu Val
            660                 665                 670

Lys Arg Thr His Leu Ala Val Val Gln Asp Leu Ala Leu Ser Gln Cys
            675                 680                 685

His Cys Val Phe Tyr Gly Gln Gln Val Glu Gly Arg Asn Phe Arg Asn
            690                 695                 700

Gln Phe Gln Pro Val Leu Arg Arg Arg Phe Val Asp Leu Phe Asn Gly
705                 710                 715                 720

Gly Phe Ile Ser Thr Arg Ser Ile Thr Val Thr Leu Ser Glu Gly Pro
                725                 730                 735

Val Ser Ala Pro Asn Pro Thr Leu Gly Gln Asp Ala Pro Ala Gly Arg
            740                 745                 750

Thr Phe Asp Gly Asp Leu Ala Arg Val Ser Val Glu Val Ile Arg Asp
            755                 760                 765

Ile Arg Val Lys Asn Arg Val Phe Ser Gly Asn Cys Thr Asn Leu
            770                 775                 780

Ser Glu Ala Ala Arg Ala Arg Leu Val Gly Leu Ala Ser Ala Tyr Gln
785                 790                 795                 800

Arg Gln Glu Lys Arg Val Asp Met Leu His Gly Ala Leu Gly Phe Leu
                805                 810                 815

Leu Lys Gln Phe His Gly Leu Leu Phe Pro Arg Gly Met Pro Pro Asn
            820                 825                 830

Ser Lys Ser Pro Asn Pro Gln Trp Phe Trp Thr Leu Leu Gln Arg Asn
```

```
                835                 840                 845
Gln Met Pro Ala Asp Lys Leu Thr His Glu Ile Thr Thr Ile Ala
    850                 855                 860
Ala Val Lys Arg Phe Thr Glu Glu Tyr Ala Ala Ile Asn Phe Ile Asn
865                 870                 875                 880
Leu Pro Pro Thr Cys Ile Gly Glu Leu Ala Gln Phe Tyr Met Ala Asn
                885                 890                 895
Leu Ile Leu Lys Tyr Cys Asp His Ser Gln Tyr Leu Ile Asn Thr Leu
            900                 905                 910
Thr Ser Ile Ile Thr Gly Ala Arg Arg Pro Arg Asp Pro Ser Ser Val
            915                 920                 925
Leu His Trp Ile Arg Lys Asp Val Thr Ser Ala Ala Asp Ile Glu Thr
        930                 935                 940
Gln Ala Lys Ala Leu Leu Glu Lys Thr Glu Asn Leu Pro Glu Leu Trp
945                 950                 955                 960
Thr Thr Ala Phe Thr Ser Thr His Leu Val Arg Ala Ala Met Asn Gln
                965                 970                 975
Arg Pro Met Val Val Leu Gly Ile Ser Ile Ser Lys Tyr His Gly Ala
            980                 985                 990
Ala Gly Asn Asn Arg Val Phe Gln Ala Gly Asn Trp Ser Gly Leu Asn
            995                 1000                1005
Gly Gly Lys Asn Val Cys Pro Leu Phe Thr Phe Asp Arg Thr Arg
    1010                1015                1020
Arg Phe Ile Ile Ala Cys Pro Arg Gly Gly Phe Ile Cys Pro Val
    1025                1030                1035
Thr Gly Pro Ser Ser Gly Asn Arg Glu Thr Thr Leu Ser Asp Gln
    1040                1045                1050
Val Arg Gly Ile Ile Val Ser Gly Gly Ala Met Val Gln Leu Ala
    1055                1060                1065
Ile Tyr Ala Thr Val Val Arg Ala Val Gly Ala Arg Ala Gln His
    1070                1075                1080
Met Ala Phe Asp Asp Trp Leu Ser Leu Thr Asp Asp Glu Phe Leu
    1085                1090                1095
Ala Arg Asp Leu Glu Glu Leu His Asp Gln Ile Ile Gln Thr Leu
    1100                1105                1110
Glu Thr Pro Trp Thr Val Glu Gly Ala Leu Glu Ala Val Lys Ile
    1115                1120                1125
Leu Asp Glu Lys Thr Thr Ala Gly Asp Gly Glu Thr Pro Thr Asn
    1130                1135                1140
Leu Ala Phe Asn Phe Asp Ser Cys Glu Pro Ser His Asp Thr Thr
    1145                1150                1155
Ser Asn Val Leu Asn Ile Ser Gly Ser Asn Ile Ser Gly Ser Thr
    1160                1165                1170
Val Pro Gly Leu Lys Arg Pro Pro Glu Asp Asp Glu Leu Phe Asp
    1175                1180                1185
Leu Ser Gly Ile Pro Ile Lys His Gly Asn Ile Thr Met Glu Met
    1190                1195                1200
Ile

<210> SEQ ID NO 11
<211> LENGTH: 3630
<212> TYPE: DNA
<213> ORGANISM: Varicella zoster
```

```
<400> SEQUENCE: 11
accaaaatgg aaaatactca gaagactgtg acagtgccca cggggcccct gggttacgtt      60
tatgcgtgcc gggttgaaga tttggatctg gaggaaattt cattttggc cgctcgtagc      120 acggactctg atttggcttt attacctttg atgcgtaatt tgaccgtgga aaaaactttt     180
acatccagcc tggcggtggt ttctggagca cgcactacgg gtcttgccgg agctggtatt    240
accttaaaac tcactaccag tcatttctat ccatctgtct ttgtctttca cggaggcaaa    300
cacgttttac ccagctccgc ggccccaaat ctcacacgcg cgtgtaacgc ggctcgagaa    360
cggtttgggt tttcacgctg ccaagggcct cctgttgacg gtgctgttga gacgaccggc    420
gctgagatat gcacccgcct tggattagag ccagaaaata caatattata cttggtggtc    480
acggcattgt ttaaggaagc cgtatttatg tgcaacgtgt ttctgcatta tggaggactc    540
gatattgttc atattaacca tggggatgtt atacgtatac cgttatttcc ggtacaactt    600
ttcatgcccg atgttaaccg tctggtaccc gacccattca acactcatca caggtctatc    660
ggagagggtt ttgtataccc aacacccttt tataacaccg ggttgtgcca tttaatacat    720
gactgtgtta ttgctcccat ggccgttgcc ttgcgcgtca gaaatgtaac tgccgtcgcc    780
cgaggagcgg cccaccttgc ttttgatgaa atcacgagg gggcagtact ccccctgac     840 attacgtaca cgtattttca gtcctcttca agtggaacca ctaccgcccg tggagcgcgt    900
cgaaacgatg tcaactccac gtctaagcct agccatcgg ggggtttga aagacggttg     960 gcgtctatta tggccgctga cacagccttg cacgcagaag ttatattcaa cactggaatt    1020
tacgaagaaa ctccaacaga tatcaaagaa tggccaatgt ttataggcat ggagggcact    1080
ttgccaaggc taaacgctct ggggtcatat accgctcgtg tggccggggt cattggtgcg    1140
atggttttca gccaaaattc tgcgttgtat ctaactgagg tggaggatag cgggatgacc    1200
gaagccaagg atgggggacc gggtccatca tttaatcgat tttaccagtt tgccggacct    1260
catttagctg cgaatcccca aacgatcga gatggccacg ttctatccag tcagtctacg     1320
ggttcatcaa acacagagtt tagcgtggat tatttggcac tcatttgtgg atttggagca    1380 ccctgttgg cgcgactgct tttttatcta gaacgctgtg acgctggtgc gtttacaggg    1440
ggtcacgggg atgcgttaaa atatgttacg gggacctttg actctgaaat tccatgtagt   1500
ttatgtgaaa acacacgcg gccggtatgc gctcacacaa cagtacaccg acttagacaa    1560
cgcatgccgc gatttggaca agccacccgt caacctattg gggtgtttgg aacaatgaac    1620
agccaatata gcgactgcga tcctctagga aactatgctc catatttaat ccttcgaaaa   1680
cccggggatc aaacggaagc agcaaaggca accatgcagg acacttatag ggctacacta    1740
gaacgcttgt ttatcgatct agaacaagag cgactactgg atcgcggtgc ccatgttct    1800 tccgagggac tatcgtctgt cattgtggat catccaacgt ttcgtcgcat attagacaca    1860
ctgcgtgcgc gtatagaaca gacaacaaca caatttatga agtgttggt tgagacccgc    1920 gattataaga tccgtgaagg attatccgaa gccacccatt caatggcgtt aacgtttgat   1980
ccatactcag gagcattttg tcccattacc aattttttag ttaaacgaac acacctagcc    2040
gtggtacaag acttagcatt aagccaatgt cattgtgtat tttacggaca gcaagttgag    2100
gggcggaact tcgtaaccaa attccaacct gttttgcggc ggcgttttgt tgacctgtt    2160 aatgggggt ttatatcaac acgctctata accgtaacat tatctgaagg tcctgtatcc   2220
gccccaaatc cgacattggg acaagacgcg cccgcgggc gtacctttga tggggatta     2280 gcgcgcgtaa gcgtggaagt tattcgggat atacgagtta aaaatagggt cgttttttca    2340
```

```
ggtaactgta caaatctctc tgaggcagcc cgggcaaggc ttgtaggcct tgcaagtgcg    2400
taccaacgcc aagaaaaaag agtggatatg ttacacgggg ccctagggtt tttgcttaaa    2460
cagtttcacg gcctgttatt tcctcggggt atgccaccaa acagtaaatc ccccaacccg    2520
cagtggtttt ggaccctgtt acaacgcaac cagatgccgg cagataaact tacacacgaa    2580
gagattacca ctattgcagc tgttaaacgg tttaccgagg aatatgcagc aataaacttt    2640
attaatctac ccccaacctg cataggagaa ttagcccagt tttatatggc aaatcttatt    2700
cttaaatact gcgatcattc acagtacctt ataaatacct taacttctat aattacgggt    2760
gccaggcgcc cgcgtgaccc atcatccgtt ttgcattgga ttcgtaaaga tgtcacgtcc    2820
gccgcggaca tagaaaccca agcaaaggcg cttcttgaaa aaacggaaaa cttaccggaa    2880
ttatggacta cggcttttac ttcaactcat ttagtccgcg cggccatgaa tcaacgtccc    2940
atggtcgttt taggaataag cattagtaaa tatcacggag cggcaggaaa caaccgcgtc    3000
tttcaggcag ggaattggag cggtttaaac gggggtaaaa atgtatgccc gctatttaca    3060
tttgatcgca ctcgccgttt tataatagca tgtcctagag gaggttttat ctgcccgta    3120 acaggtccct cgtcgggaaa tcgagaaacc accctatccg accaagttcg cggtataatt    3180
gtcagtggcg gggccatggt tcaattagcc atatacgcca cggttgtgcg tgcagtgggc    3240
gctcgagcac aacatatggc atttgacgac tggttaagtc ttacagacga tgagttttta    3300
gccagagact tggaggagtt acacgaccag attatccaaa ccctggaaac gccctggacc    3360
gtagaaggcg ctctagaagc agtaaagatt ctagatgaaa aaacgacagc gggagatggg    3420
gaaaccccca caaacctagc atttaattt  gattcttgtg aaccaagcca tgacaccaca    3480
tctaacgtat taaacatttc agggtcaaac atttcagggt caactgtccc tggtcttaaa    3540
cgaccccccg aagatgacga actctttgat cttagtggta ttcccataaa acatgggaac    3600
attacaatgg aaatgattta acctccctct                                    3630
```